(12) United States Patent
Martínez Lamas et al.

(10) Patent No.: US 11,230,694 B2
(45) Date of Patent: Jan. 25, 2022

(54) ANTIMICROBIAL STRAIN

(71) Applicants: SERVIZO GALEGO DE SAÚDE (SERGAS), Santiago de Compostela (ES); UNIVERSIDADE DE SANTIAGO DE COMPOSTELA (USC), Santiago de Compostela (ES)

(72) Inventors: Lucía Martínez Lamas, Vigo (ES); Maximiliano Álvarez Fernández, Vigo (ES); Pedro Diz Dios, Santiago de Compostela (ES); Jacobo Limeres Posse, Santiago de Compostela (ES)

(73) Assignees: SERVIZO GALEGO DE SAÚDE (SERGAS), Santiago de Compostela (ES); UNIVERSIDADE DE SANTIAGO DE COMPOSTELA (USC), Santiago de Compostela (ES)

( * ) Notice: Subject to any disclaimer, the term of this patent is extended or adjusted under 35 U.S.C. 154(b) by 74 days.

(21) Appl. No.: 16/463,348

(22) PCT Filed: Nov. 24, 2017

(86) PCT No.: PCT/EP2017/080416
§ 371 (c)(1),
(2) Date: May 22, 2019

(87) PCT Pub. No.: WO2018/096118
PCT Pub. Date: May 31, 2018

(65) Prior Publication Data
US 2020/0002777 A1  Jan. 2, 2020

(30) Foreign Application Priority Data
Nov. 24, 2016 (EP) .................................. 16200473
Nov. 24, 2016 (EP) .................................. 16382565

(51) Int. Cl.
*C12N 1/20* (2006.01)
*A23L 33/135* (2016.01)
*A61K 9/00* (2006.01)
*C12R 1/46* (2006.01)

(52) U.S. Cl.
CPC ............ *C12N 1/205* (2021.05); *A23L 33/135* (2016.08); *A61K 9/0053* (2013.01); *C12R 2001/46* (2021.05)

(58) Field of Classification Search
None
See application file for complete search history.

(56) References Cited

FOREIGN PATENT DOCUMENTS

EP  2 612 904 A2  7/2013
WO  03/070919 A1  8/2003

OTHER PUBLICATIONS

Bresciani et al., "Buccal Health and Quality of Life," *Salusvita*, Bauru 24(1):137-148, 2005.
Forssten et al., "*Streptococcus mutans*, Caries and Simulation Models," *Nutrients* 2:290-298, 2010.
Sánchez et al., "Structure, viability and bacterial kinetics of an in vitro biofilm model using six bacteria from the subgingival microbiota," *J. Periodont. Res.* 46:252-260, 2011.
Terai et al., "Screening of Probiotic Candidates in Human Oral Bacteria for the Prevention of Dental Disease," *PLoS ONE* 10(6):e0128657, 2015. (20 pages).

*Primary Examiner* — Padmavathi Baskar
(74) *Attorney, Agent, or Firm* — Seed Intellectual Property Law Group LLP

(57) ABSTRACT

The present invention belongs to the field of the biotechnology, and relates to novel Streptococcusbacteria which are useful as antimicrobial agents, particularly against caries and periodontal disease. The invention relates to compositions and functional food comprising the novel bacteria. In particular, the present invention relates to a novel bacterial strain, deposited at the Colección Española de Cultivos Tipo, with accession number CECT 9174, which has proven to be useful in the prevention and treatment of caries and periodontal disease.

16 Claims, 18 Drawing Sheets

Figure 7. A
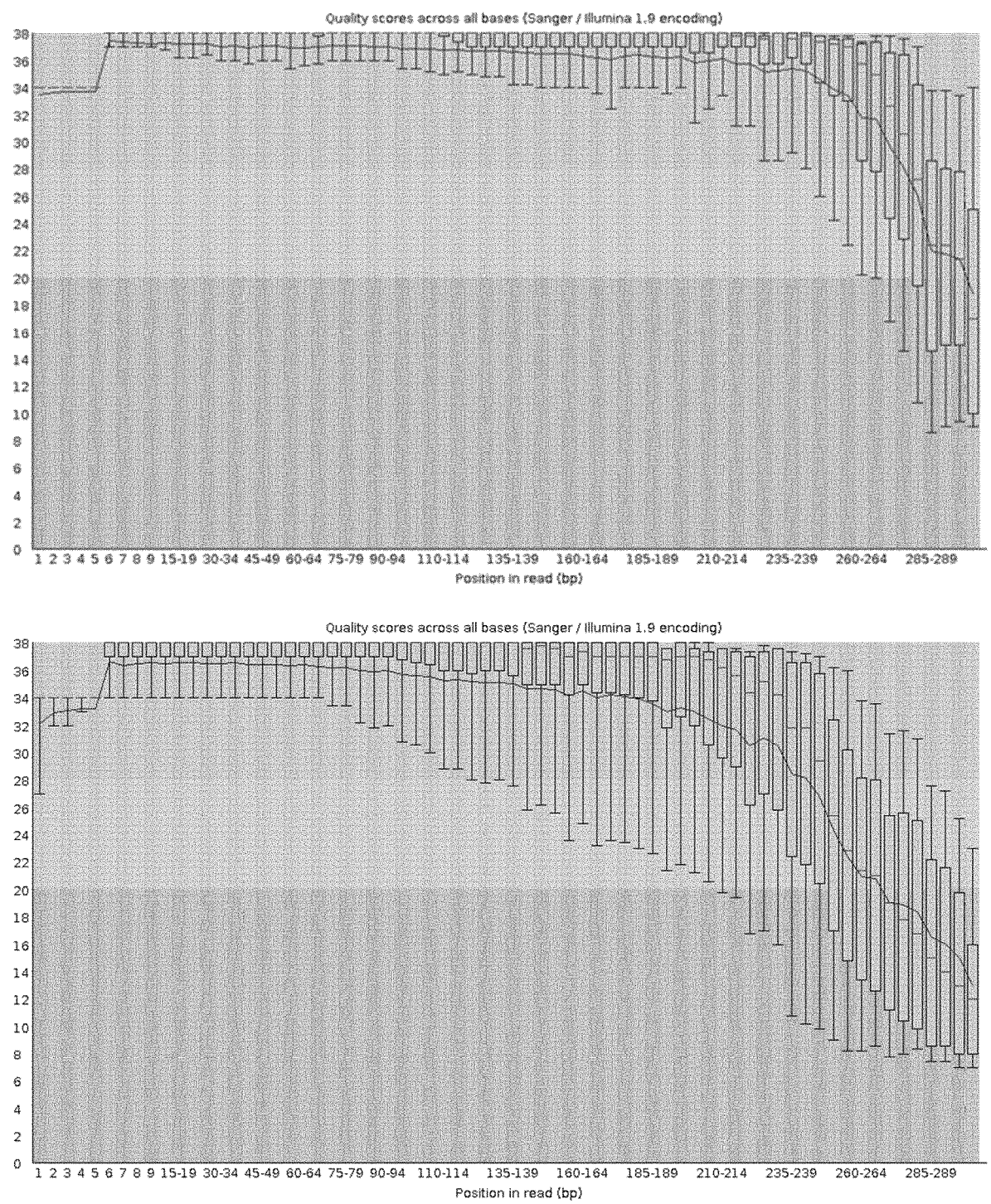

Figure 7. B
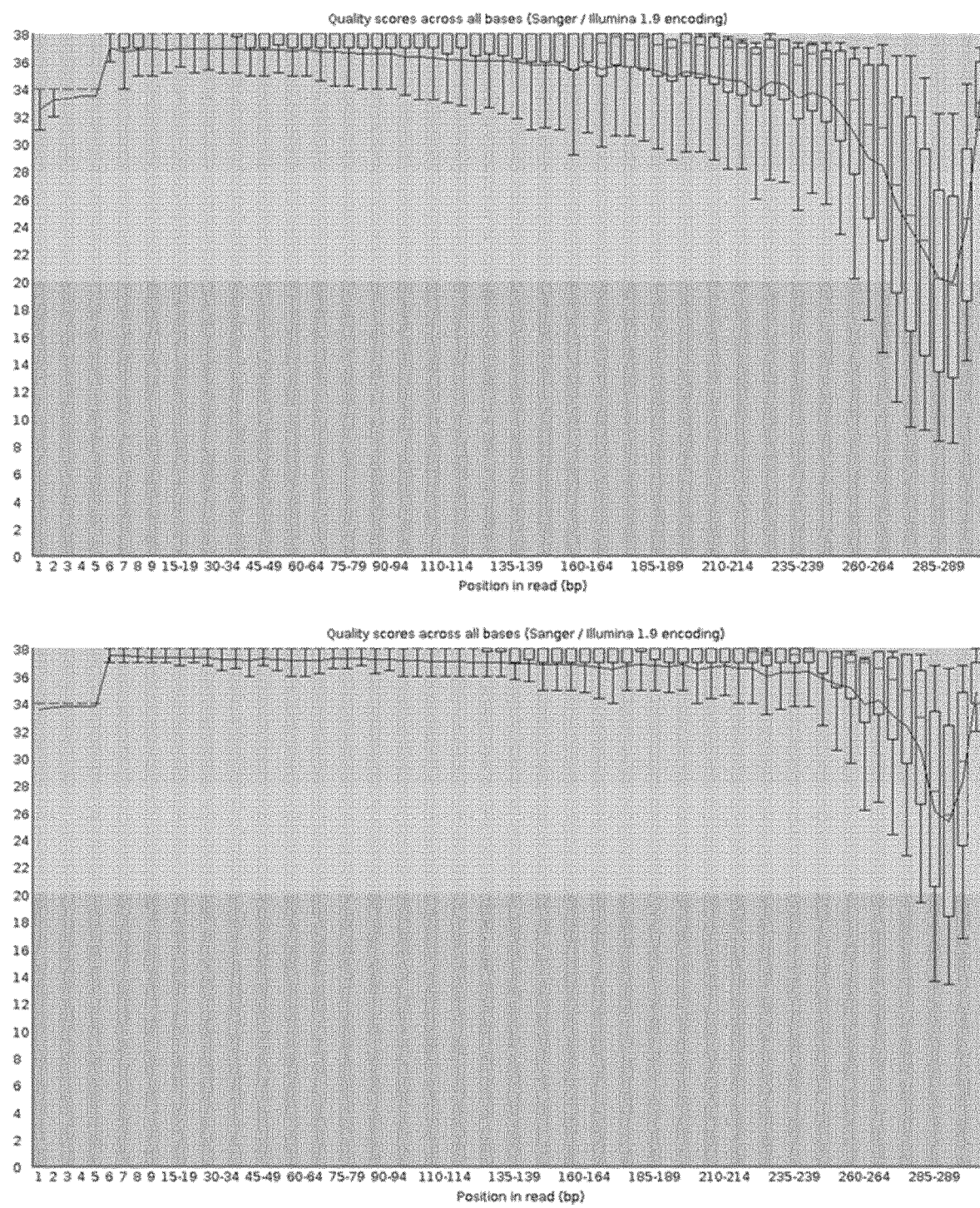

Figure 8. A
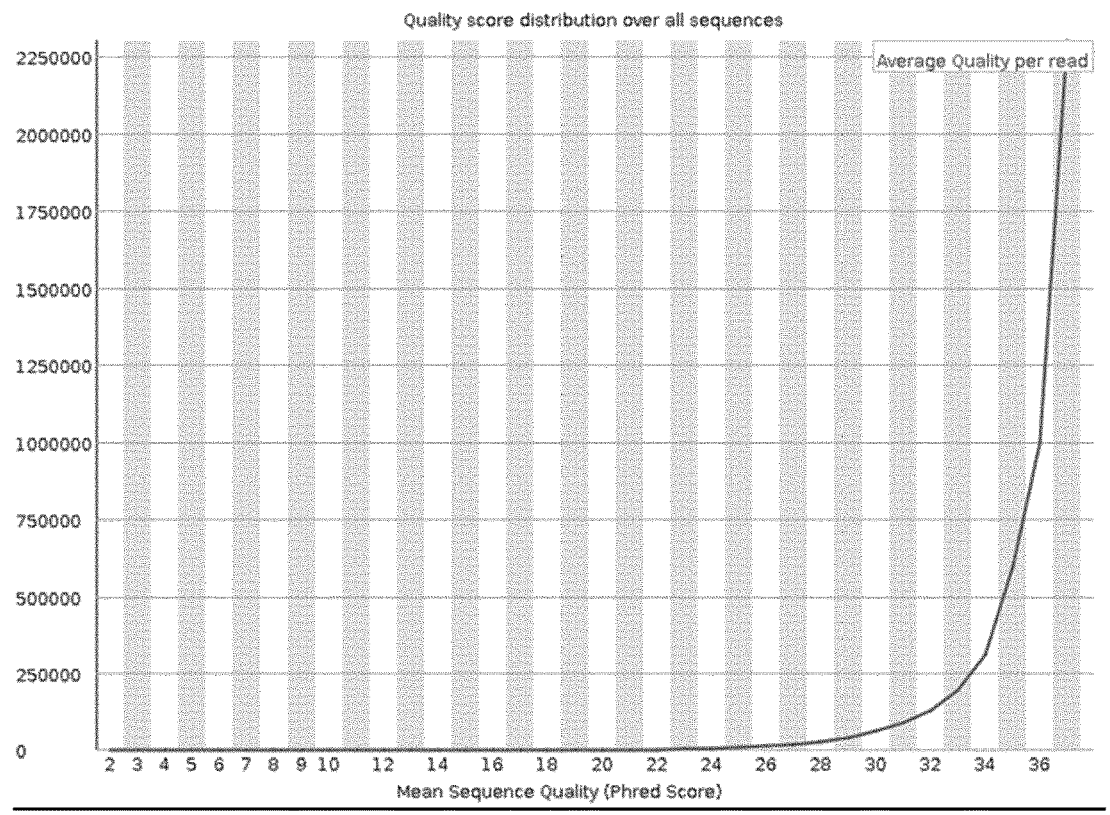
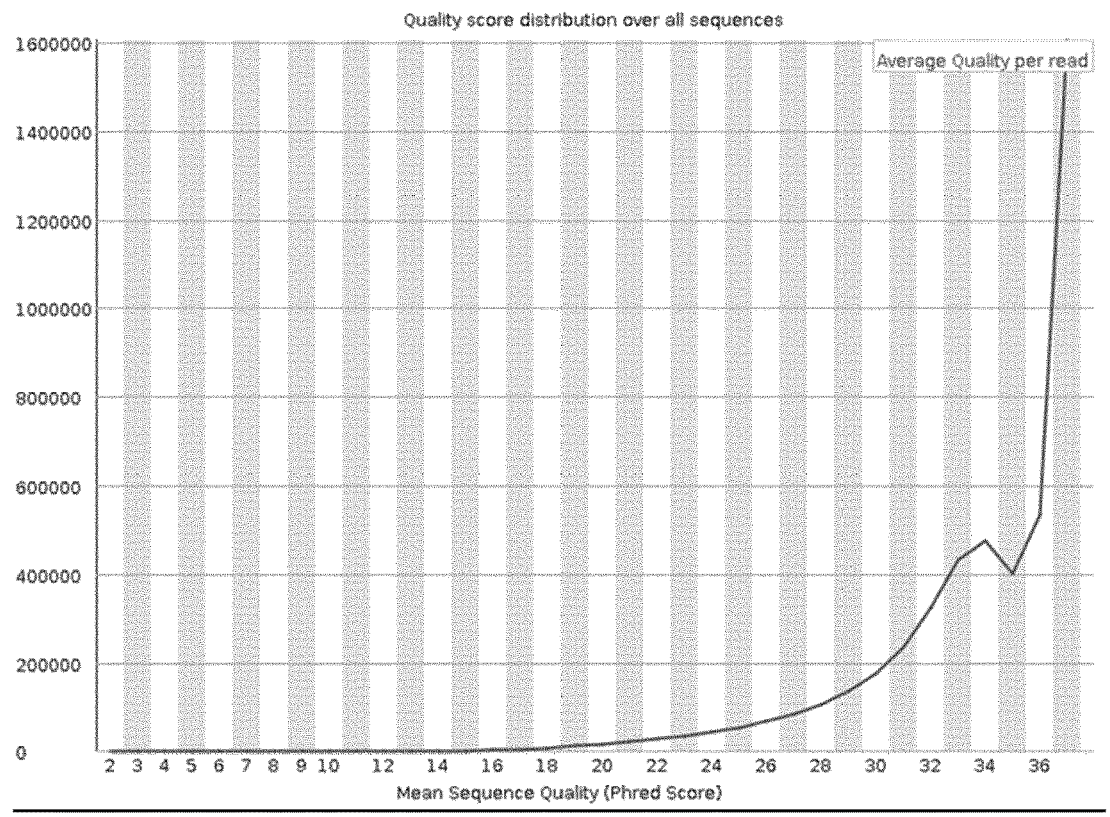

Figure 8. B
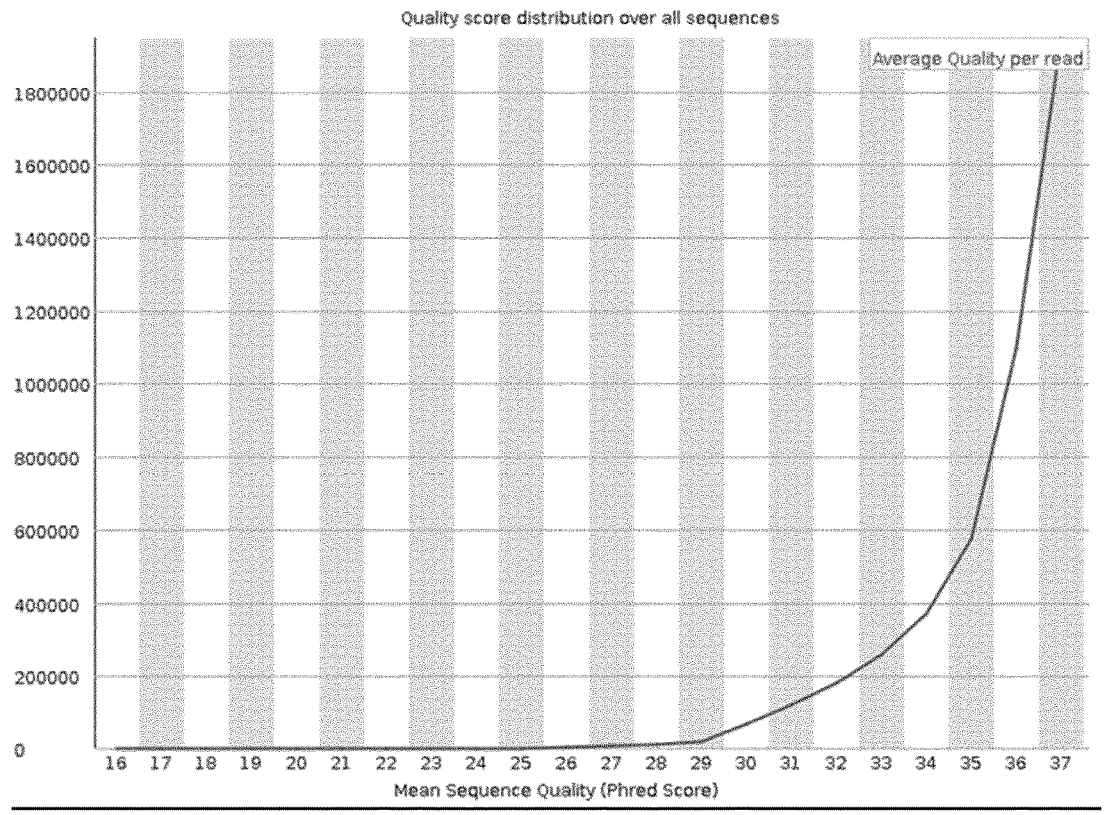
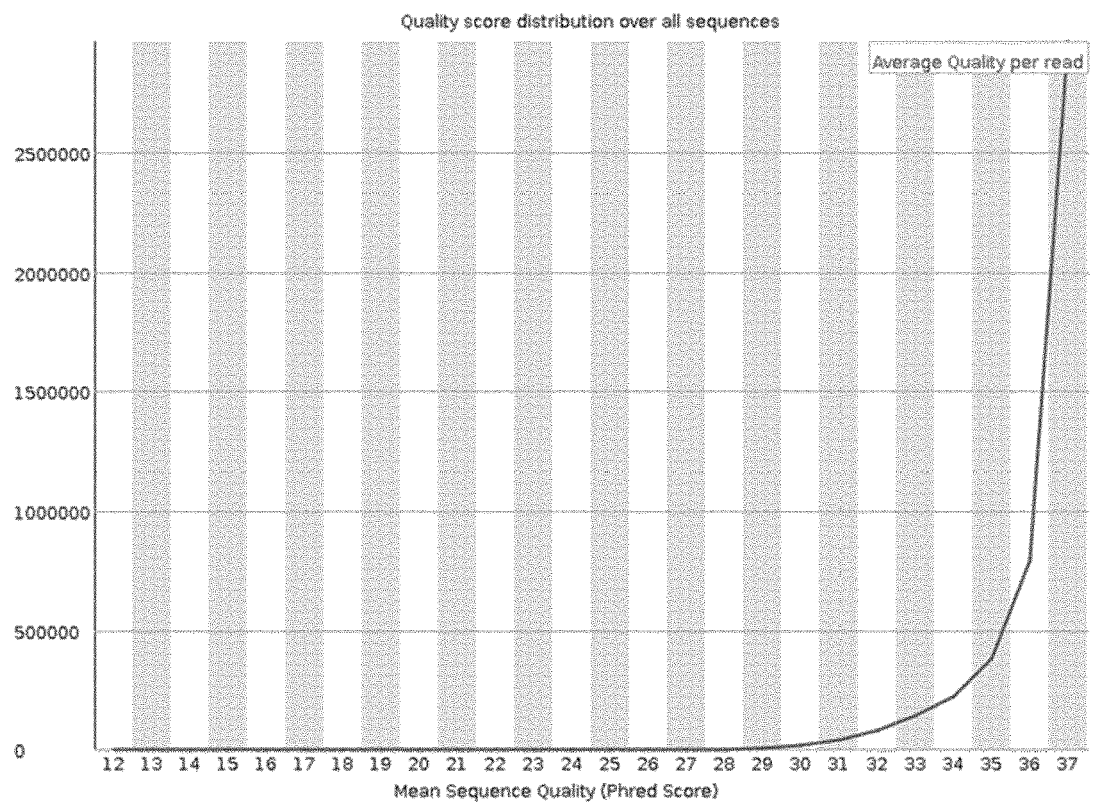

Figure 9. A
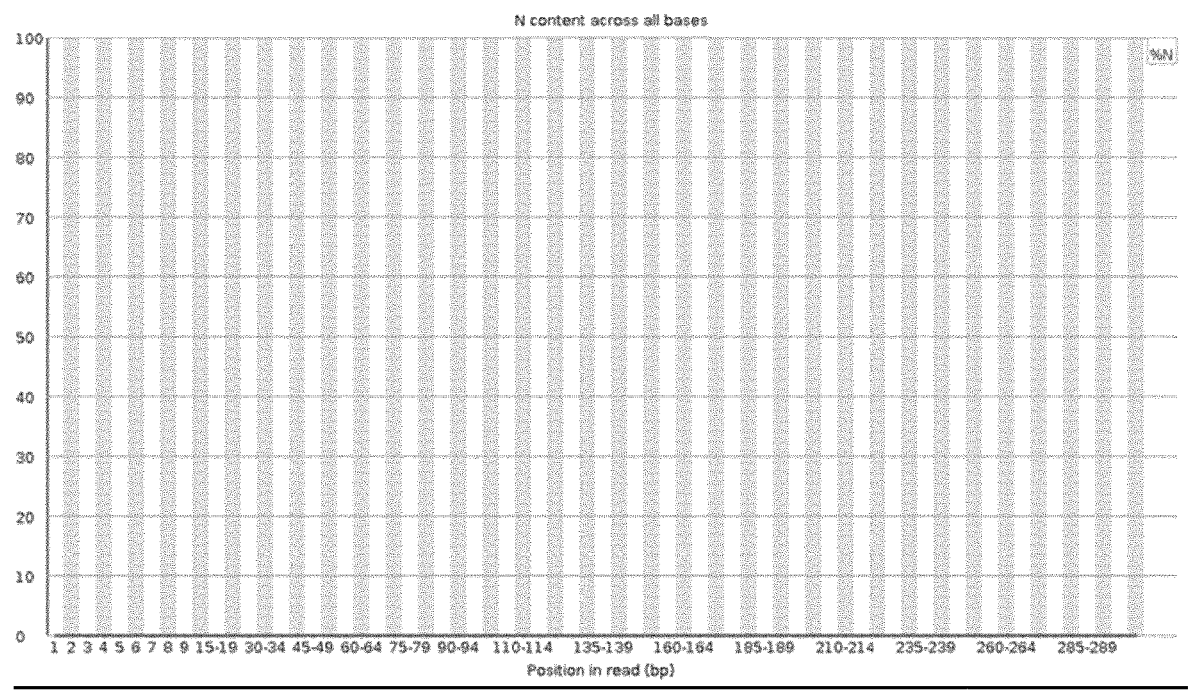
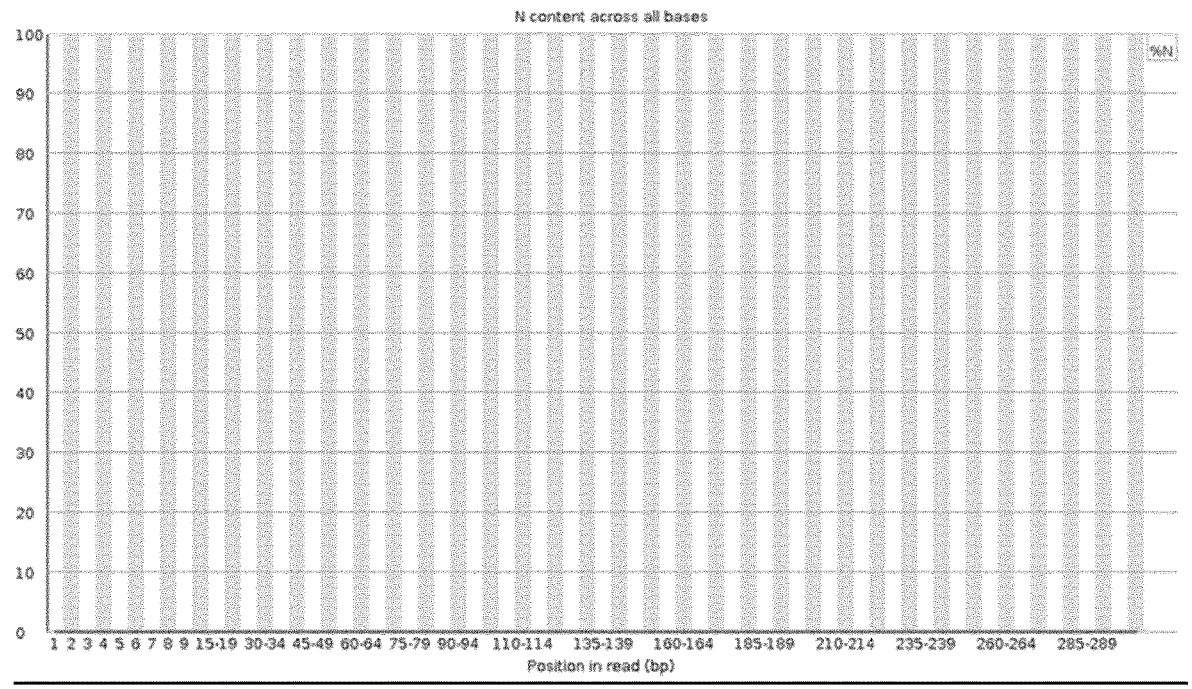

Figure 9. B
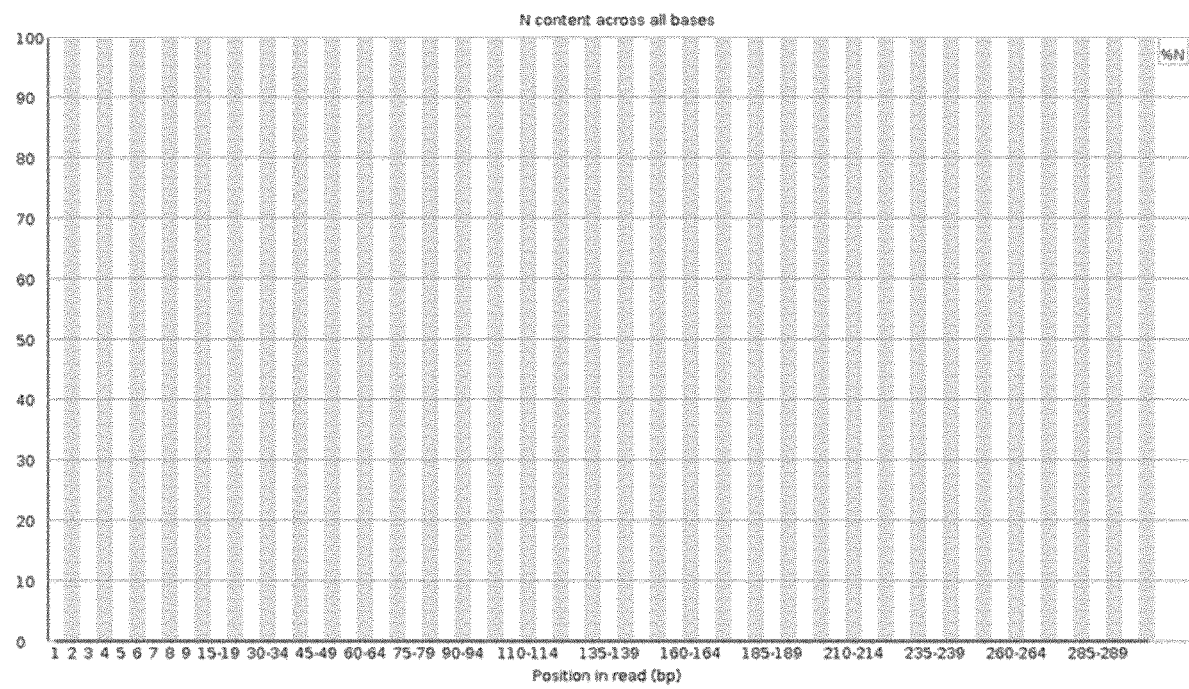
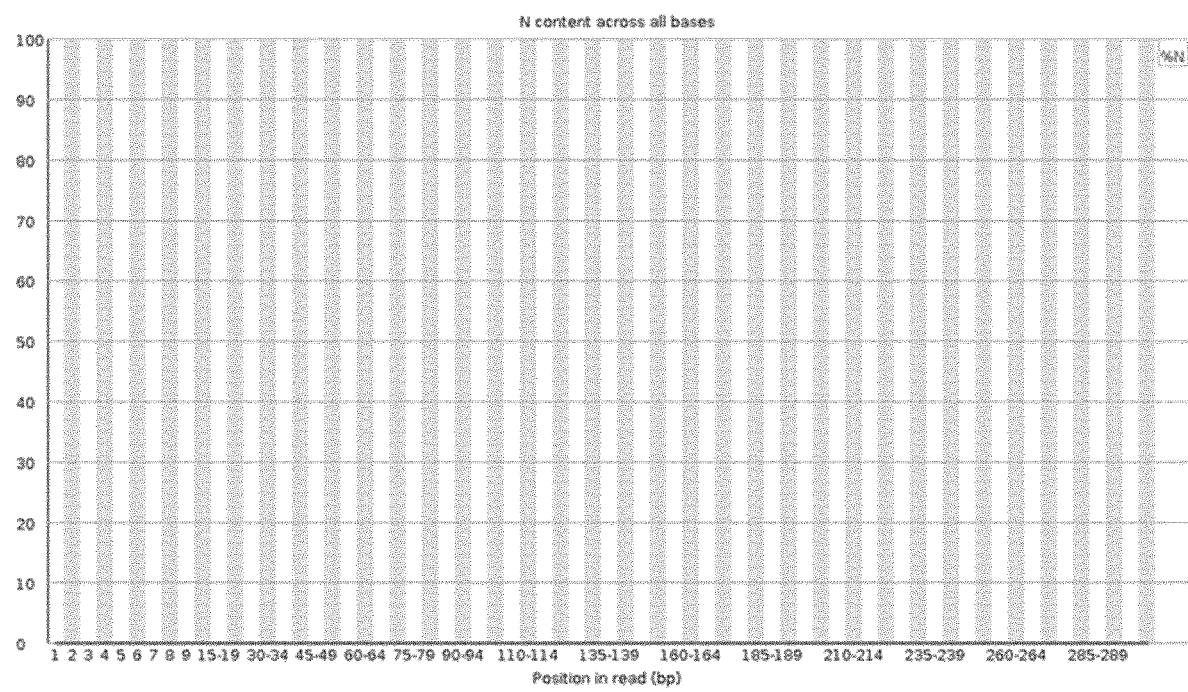

Figure 10. A
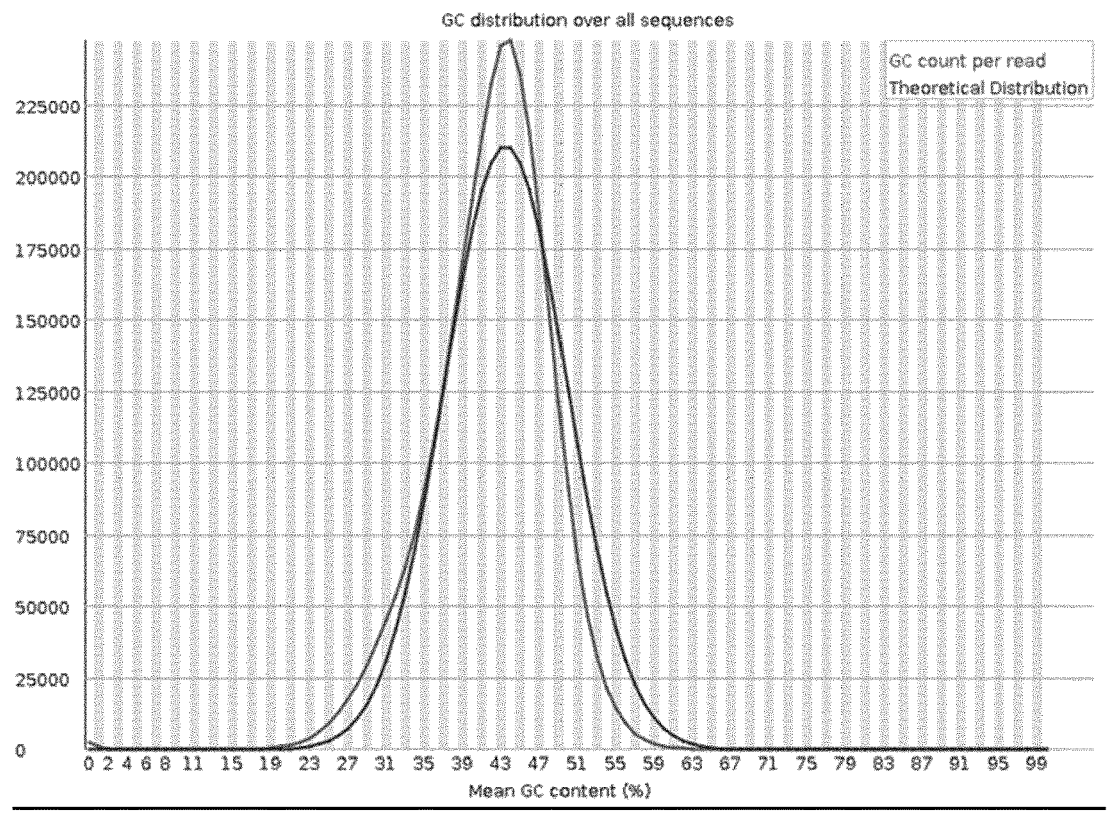
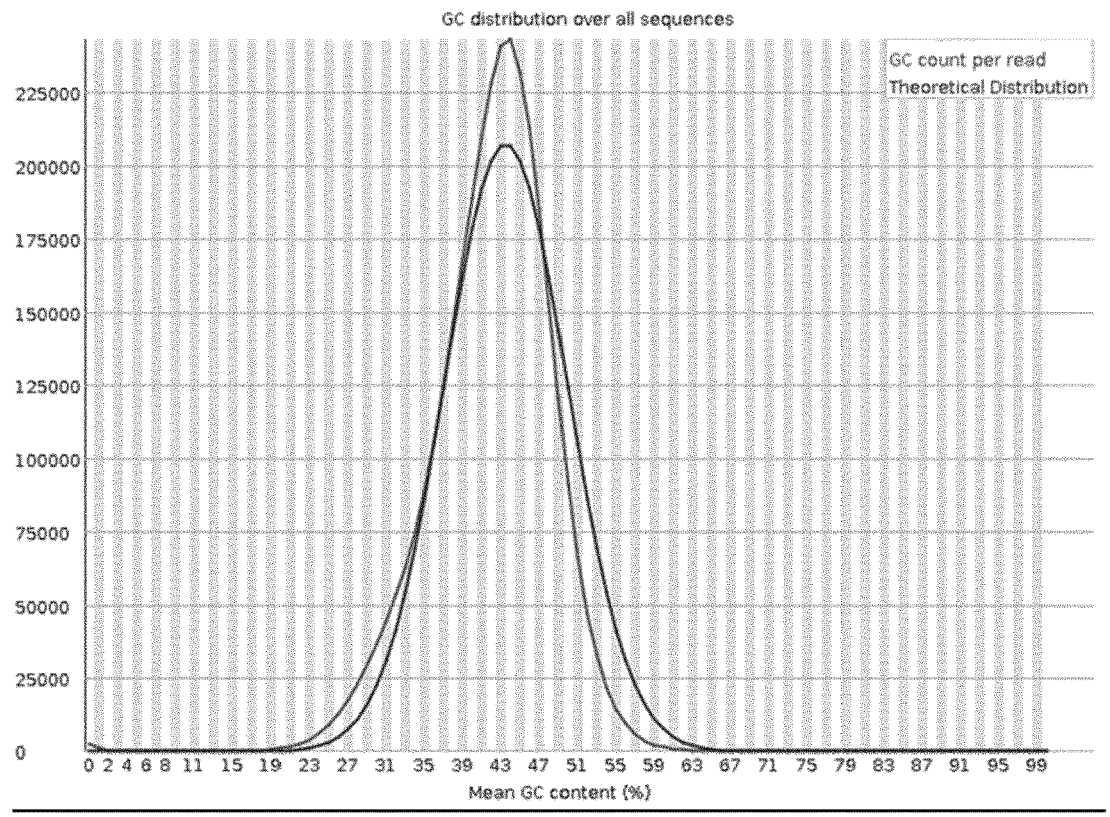

Figure 10. B
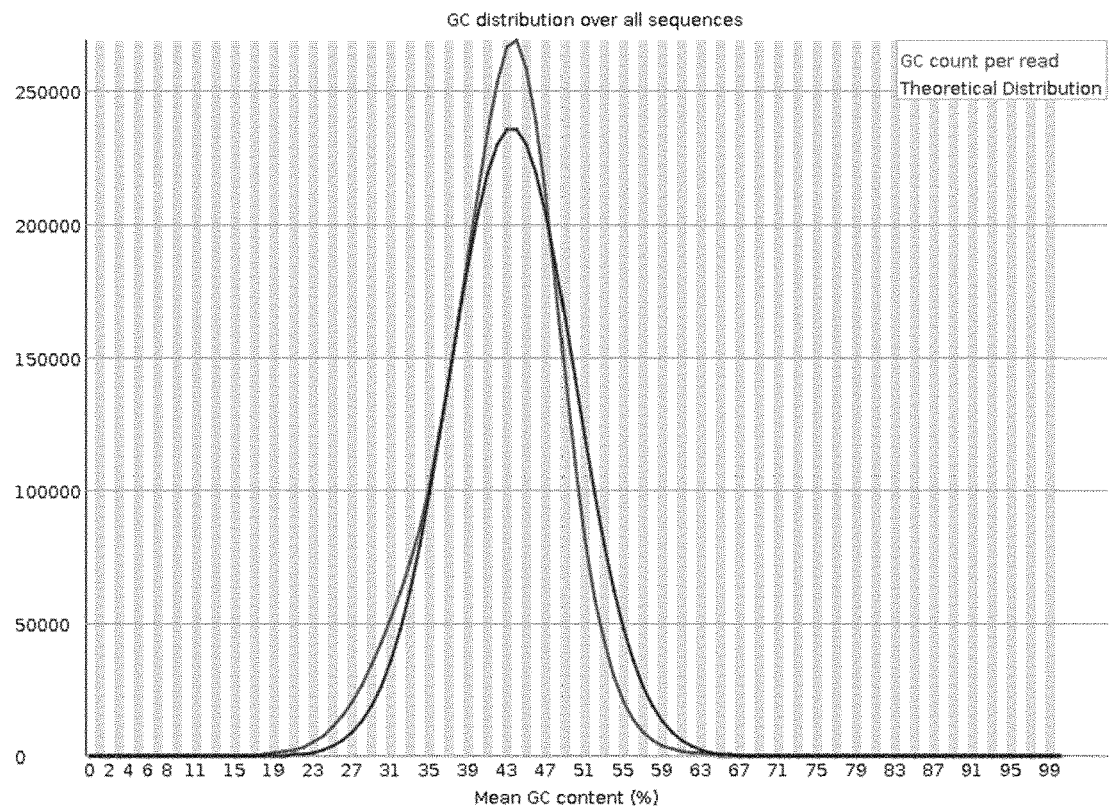
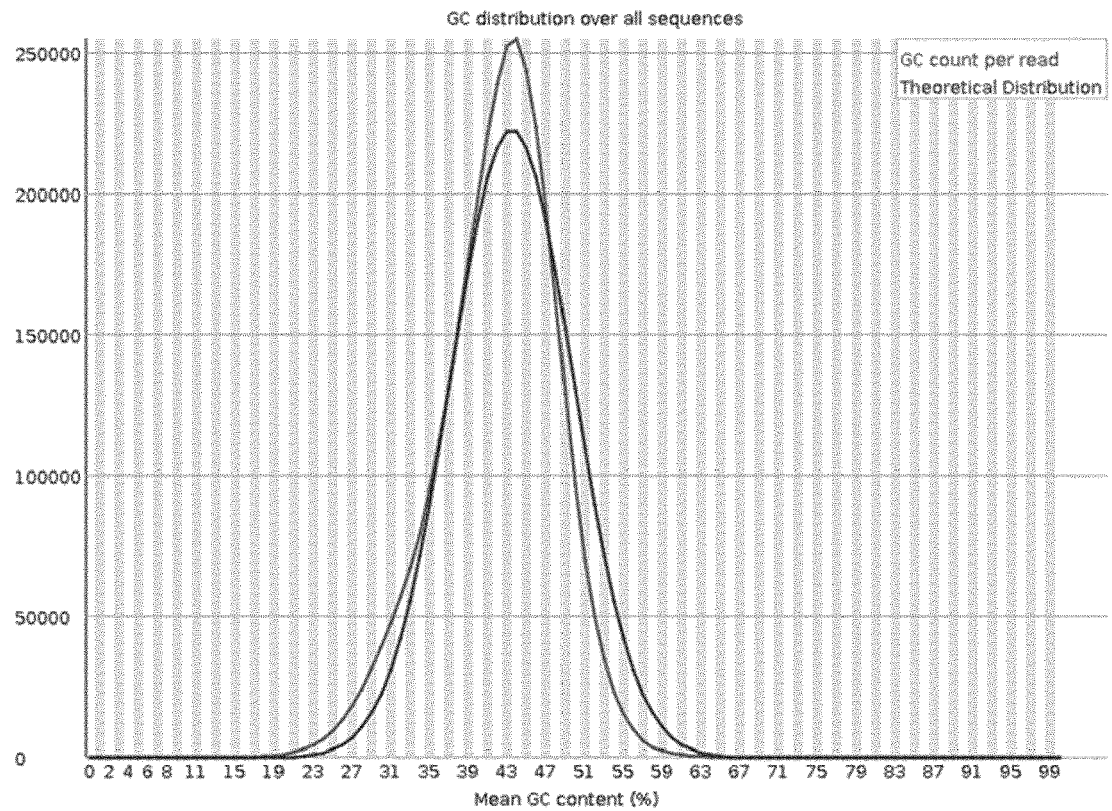

ANTIMICROBIAL STRAIN

FIELD OF THE INVENTION

The present invention belongs to the field of the biotechnology, and relates to novel *Streptococcus* bacteria which are useful as antimicrobial agents, particularly as anticaries agents. The invention relates to compositions and functional food comprising the novel bacteria.

BACKGROUND OF THE INVENTION

According to the 2003 annual WHO report, oral health is integrated with the general health of people and it is a determinant of quality of life (Bresciani, E. et al., Buccal health and quality of life, *Salusvita*, Bauru, v. 24, n. 1, p. 137-148, 2005).

Caries and periodontal disease are two major diseases with very high prevalence, which affect the oral health of many people around the world. According to the National Institute of Dental and Craniofacial Research, 92% of adults aged 20 to 64 have had dental caries in their permanent teeth (Data Source: The National Health and Nutrition Examination Survey (NHANES)). According to the same source, 47% of adults aged 30 years and older have some form of periodontal disease.

Caries and periodontal disease are caused by pathogenic bacteria causing infection in the oral cavity. For Instance, *Streptococcus oralis*, *Veillonella parvula*, *Actinomyces naeslundii*, *Fusobacterium nucleatum*, *Porphyromonas gingivalis* and *Aggregatibacter actinomycetemcomitans* may be involved in dental plaque accumulation which promotes periodontal disease.

*S. mutans* gives its name to a group of seven closely related species collectively referred-to as the mutans streptococci. It has a crucial role in the development of caries. Usually, the appearance of *S. mutans* in the tooth cavities is followed by caries after 6-24 months (Forssten, S. D. et al., *Streptococcus mutans*, Caries and Simulation Models, Nutrients 2010, 2, 290-298).

There are several methods available for the treatment of caries and periodontal disease related infectious complications, including antibiotic therapy. However, antibiotics destroy both useful and harmful bacteria in the oral cavity, leading to undesired microbial imbalances.

The use of bacteria for the treatment of infectious diseases of the oral cavity, such as caries and periodontal disease, has been explored in the last years.

For instance, WO 20031070919 discloses the use of BUS-producing *Streptococcus salivarius* strains with activity against mutans streptococci (MS) dental caries causing organisms including *S. salivarius*.

However, *S. salivarius* strains are virtually absent from dental surfaces, and it has been shown to be present only on the tongue surface. Therefore, a strain which can adhere to the dental surfaces would be desirable, since it would be able to compete with pathogenic bacteria and therefore prevent and/or treat infections of the oral cavity such as caries and periodontal disease.

Accordingly, there is a need of an anti-microbial agent which is present in the oral microflora of healthy subjects, particularly on dental surfaces, preferably in dental plaque, and which has an antimicrobial effect against several pathogenic microorganisms involved in oral infections, such as *S. mutans*, *A. naeslundii*, *V. parvula* and *A. actinomycetemcomitans*, useful in the treatment of oral infections such as caries and/or periodontal disease.

SUMMARY OF THE INVENTION

The present invention belongs to the field of microbiology and, in particular, to a specific bacterial strain suitable for use in the prophylactic or therapeutic treatment of infectious diseases of the oral cavity.

In a first aspect, the present invention provides a bacterial strain deposited at the Colección Española de Cultivos Tipo (CECT) by Servicio Galego de Saúde (SERGAS), on Jul. 20, 2018, with accession number CECT 9174.

The present invention further provides an extract and a supernatant derived from the culture of the bacterial strain of the present invention.

In addition, the present invention provides the bacterial strain of the present invention, the extract or the supernatant for use as a medicament, in particular for use as an antimicrobial medicament, preferably in the prophylactic or therapeutic treatment of infectious diseases of the oral cavity, such as caries and/or periodontal disease.

The present invention also provides the bacterial strain of the present invention, the extract or the supernatant for use as a probiotic, medical food composition or functional food-to improve oral health. It is also subject of the present invention a pharmaceutical composition and/or an oral health composition that comprises the bacterial strain of the present invention, with deposit number CECT 9174, and/or the extract and/or the supernatant of the present invention. The present invention further provides the use of the pharmaceutical composition or oral health composition or functional food of the present invention as a medicament, in particular in the prophylactic or therapeutic treatment of infectious diseases of the oral cavity, such as caries and/or periodontal disease.

*tans* and *Porphyromonas gingivalis*; (E,F) the novel *Streptococcus* sp. strain, *Veillonella parvula, Actinomyces naeslundii, Fusobacterium nucleatum, Aggregatibacter actinomycetemcomitans* and *Porphyromonas gingivalis*. The bacterial disposition as well as the three-dimensional structure of the different biofilms show (A,B) a compact biofilm well structured; (C,D) a well-structured biofilm but with lower density than that observed in images A,B; (E,F) absence of a well-structured community, being the novel *Streptococcus* spp. strain the bacterial-species predominant over the hydroxyapatite disks surface. Magnification: (A,C, E): 500×; (B,D,F): 1,000×.

Figure 6:
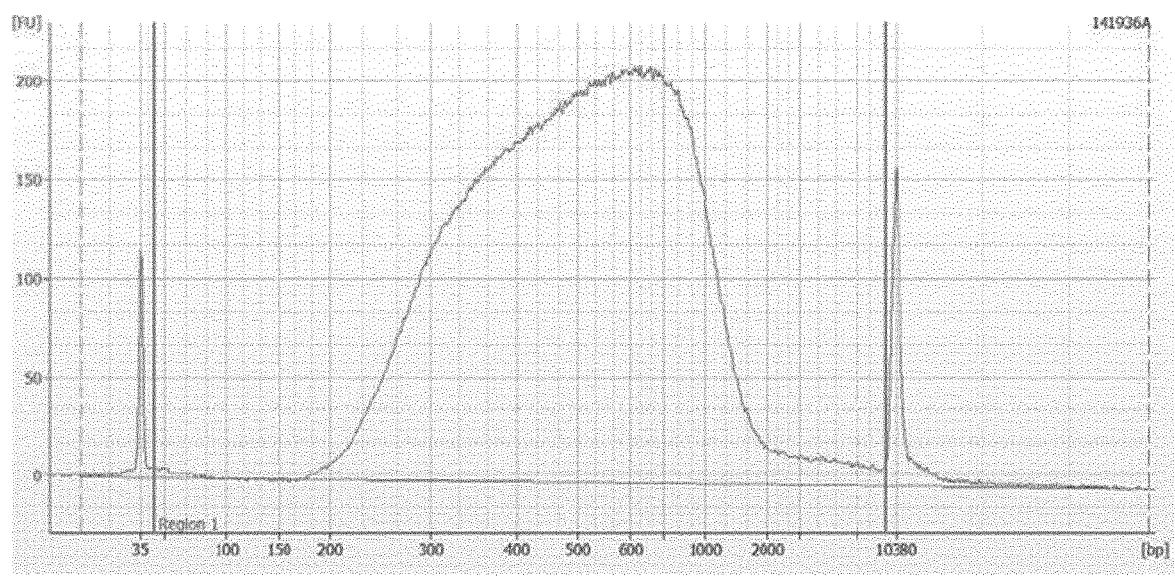

FIG. 6. Profile of Agilent 2100 Bioanalyzer for the resulting library.

FIG. 7. Average quality and interquartile range and mean for each of the positions of the readings. Sample in the direction R1 is shown on the left side and sample in the direction R2 is shown on the right side. Panel A is for raw sequences and panel B is for trimmed sequences.

FIG. 8. Depiction of the average quality with respect to the number of readings having said average quality. Sample in the direction R1 is shown on the left side and sample in the direction R2 is shown on the right side. Panel A is for raw sequences and panel B is for trimmed sequences.

FIG. 9. Depiction of the amount of indeterminations (N) in each of the positions of the sequences that have been examined. Sample in the direction R1 is shown on the left side and sample in the direction R2 is shown on the right side. Panel A is for raw sequences and panel B is for trimmed sequences.

FIG. 10. GC content distribution of the sequences (in red) with respect to a theoretical distribution. Sample in the direction R1 is shown on the left side and sample in the direction R2 is shown on the right side. Panel A is for raw sequences and panel B is for "trimmed" sequences.

Figure 11:
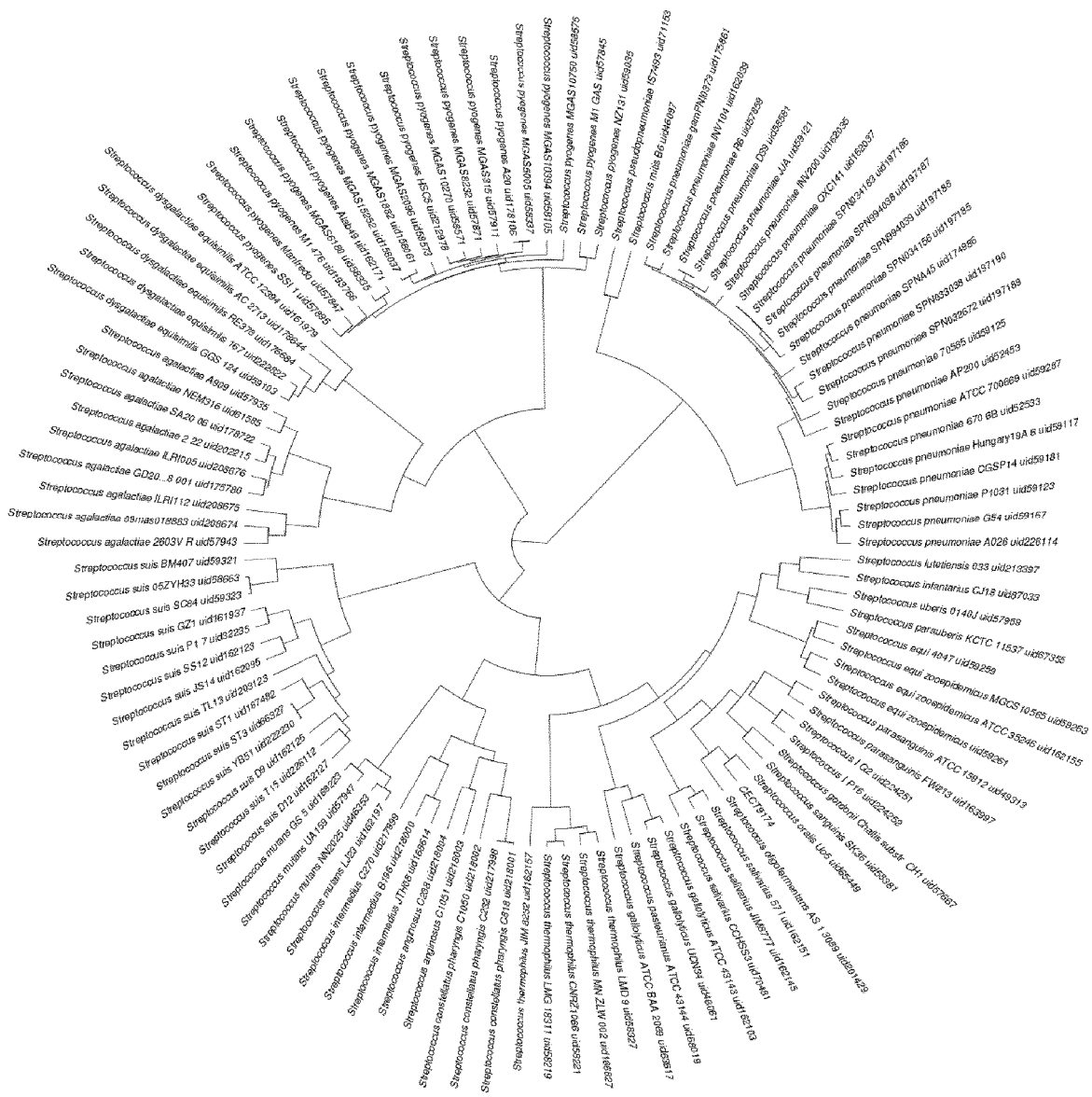

FIG. 11. Topology based on the Average Nucleotide Identity (ANI) for locating the CECT 9174 strain under study.

Figure 12:
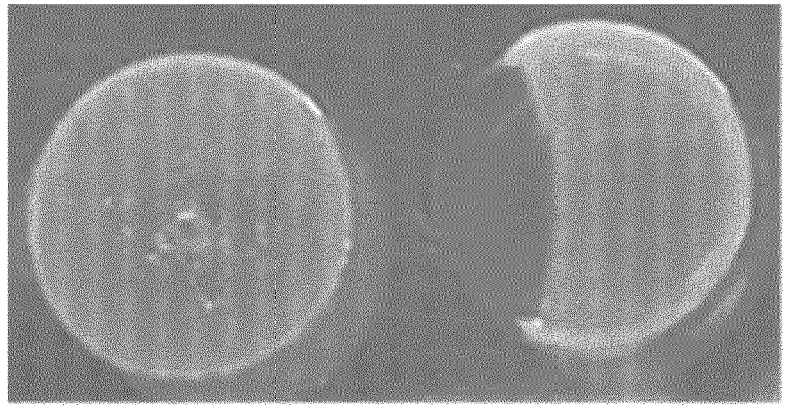

FIG. 12. Results of the plate competition test on BHI plates.

Figure 13:
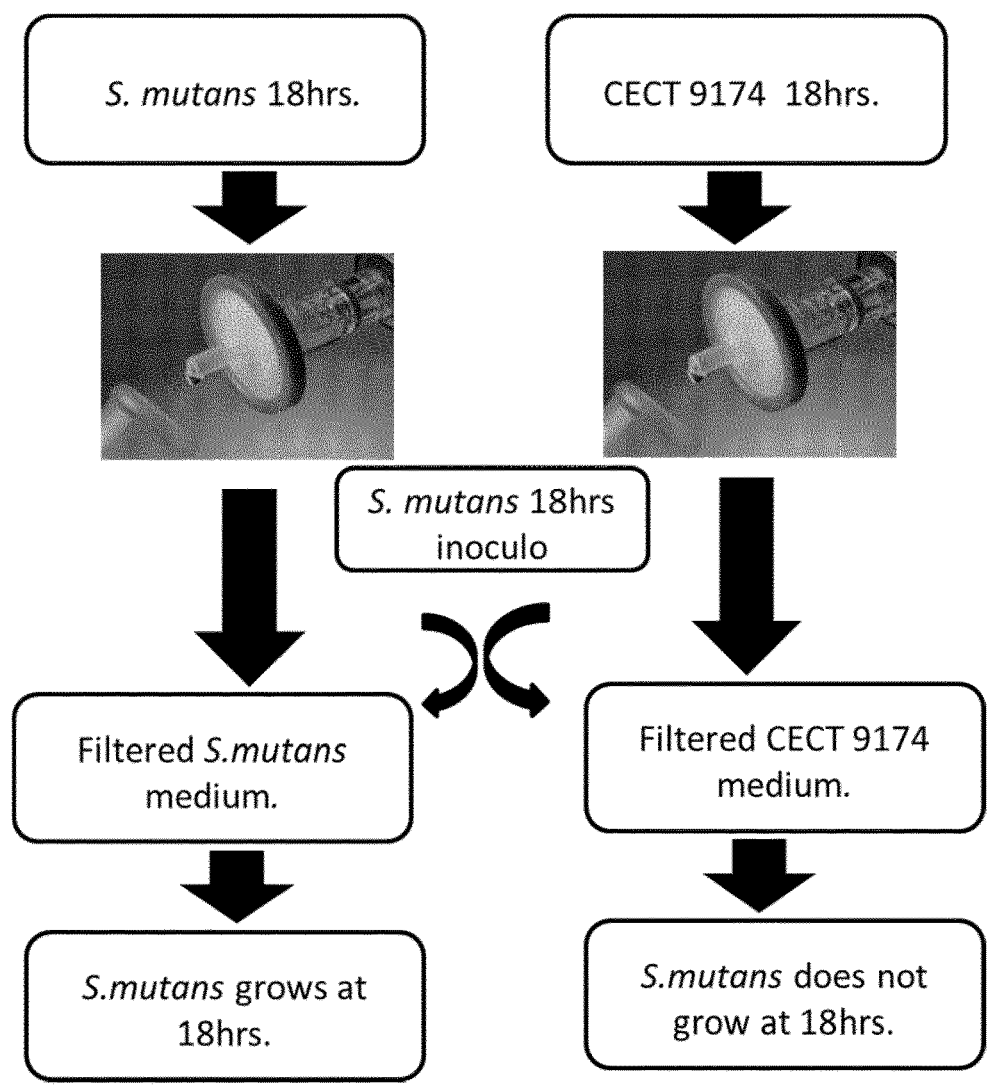

FIG. 13. Design of the supernatant inhibition assay.

Figure 14:
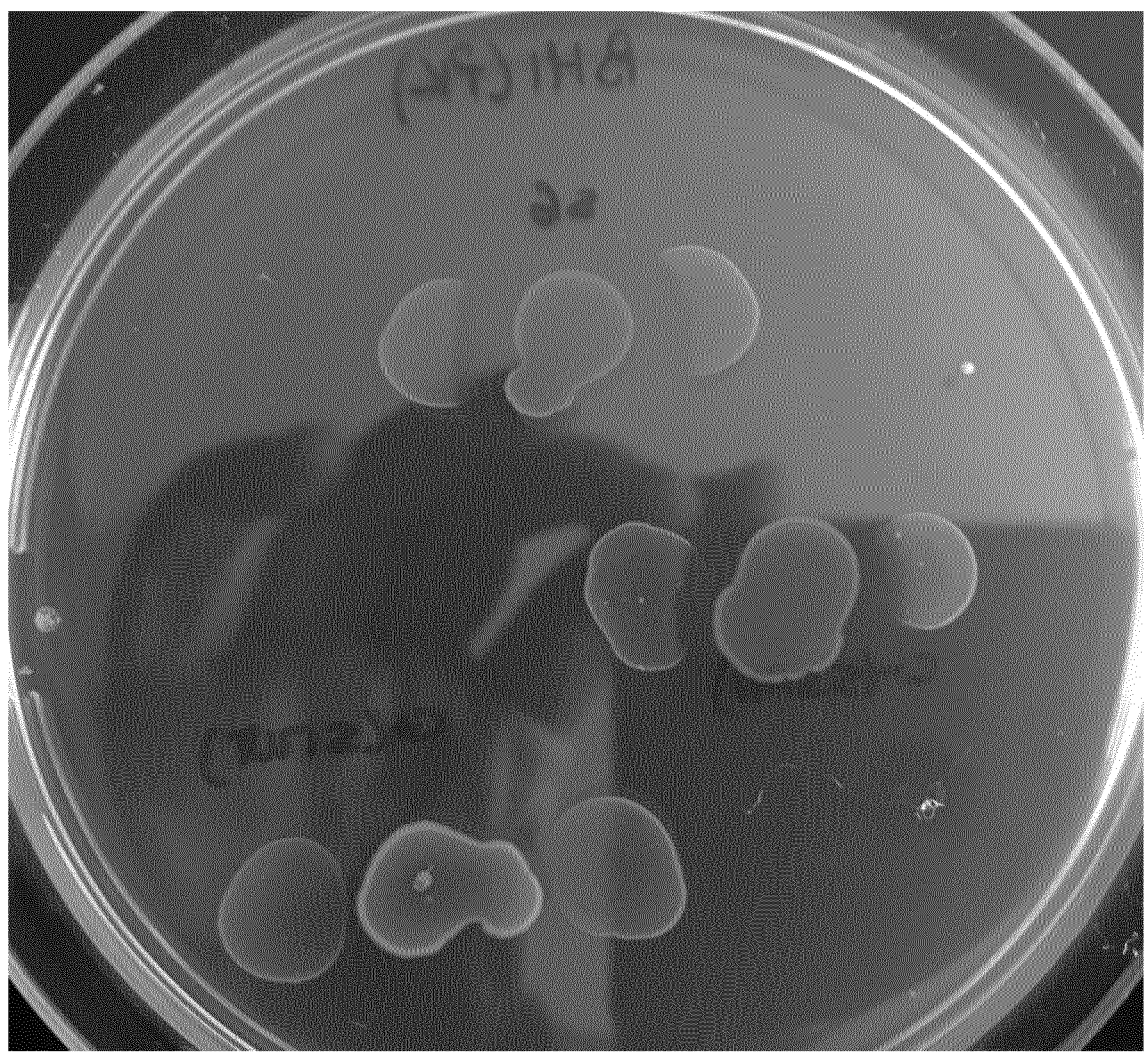

FIG. 14. The inhibitory activity of S. CECT 9174 is not affected by the proteinase K activity. A) S. CECT 9174 (middle), PBS (right side), proteinase K (left side). *S. mutans* left and right side. B) Negative control *S. dentisani*, PBS right and left side, *S. mutans* right and left side. C) Positive control *S. dentisani*, Proteinase K right and left side, *S. mutans* right and left side.

Figure 15:
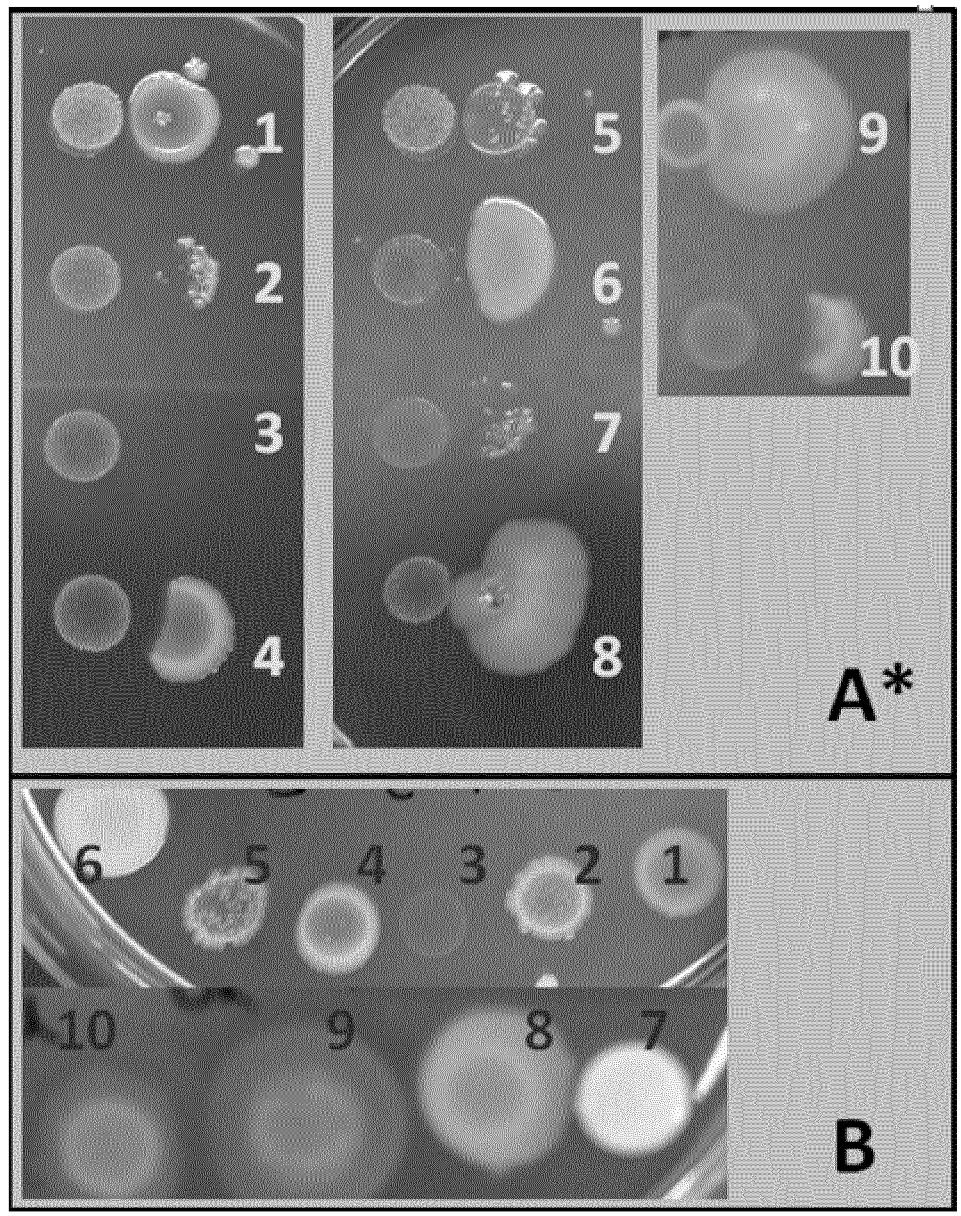

FIG. 15. A) Shows the inhibition assay and B) shows the growth control. 1. *L. ivanovii*, 2. *S. pyogenes*, 3. *S. pneumoniae*, 4. *S. galactiae*, 5. *Lactobacillus*, 8. *S. aureus*, 7. *S. warnerii*, 8. *E. coli*. CECT 9174 inhibits: *S. pyogenes, S. pneumoniae, S. agalacdae, S. aureus, S. warnerii, S. mutans*.

Figure 16:
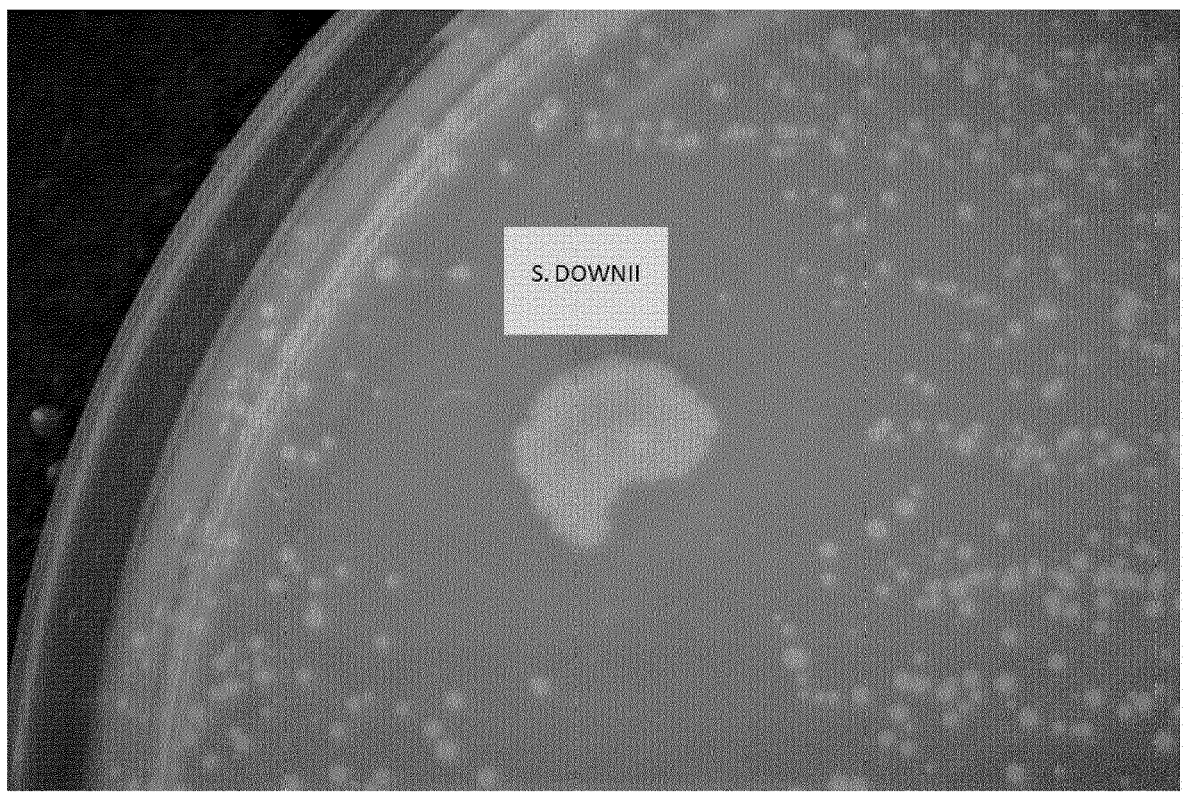

FIG. 16. CECT 9174 inhibition over *Fusobacterium nucleatum*.

DETAILED DESCRIPTION OF THE INVENTION

Definitions

Unless otherwise defined, all technical and scientific terms used herein have the meaning commonly understood by one skilled in the art to which this invention belongs.

As used herein, the term "about" means the indicated value ±1% of its value, or the term "about" means the indicated value ±2% of its value, or the term "about" means the indicated value ±5% of its value, or the term "about" means the indicated value ±10% of its value, or the term "about" means the indicated value ±20% of its value, or the term "about" means the indicated value ±30% of its value; preferably the term "about" means exactly the indicated value (±0%).

The terms "treatment" or "therapy" encompass both prophylactic and curative methods of treating disease, since both are directed to the maintenance or restoration of health. Irrespective of the origin of pain, discomfort or incapacity, its relief, by the administration of an appropriate agent, is to be construed as therapy or therapeutic use in the context of the present application.

It is understood that "infection" in the present invention is that pathology caused by the invasion of any host tissue by pathogenic bacteria. It is understood as "infectious diseases of the oral cavity" as those bacterial infections affecting the hard and/or soft oral tissues, such as for example infections which occur in teeth and/or gums and/or the tongue and/or the mucosa lining the lips, cheeks and gums. Examples of infectious diseases of the oral cavity are caries (dental cavities or tooth decay) and periodontal (gum) disease (periodontitis).

In the context of the present invention, an "anti-microbial medicament" is a substance, composition, microorganism or microorganism culture able to inhibit the growth of other microorganisms, in particular of pathogenic microorganisms.

In the context of the present invention, a "medical food composition" is understood as a food composition specially formulated and intended for the dietary management of a disease that has distinctive nutritional needs that cannot be met by normal diet alone.

In the context of the present invention the term "probiotic" refers to live microorganisms which provide health benefits when consumed. The live microorganisms may be added to foods (e.g., dairy products such as milk, yogurts, etc.), dietary supplements or that may be taken alone. The probiotics remain active and exert their effects on the subject that takes them. When taken in enough quantities, the probiotics have beneficial effects, in the particular case of the present invention, beneficial effects on oral health, in the treatment and/or prevention of infections of the oral cavity, such as cares.

In the context of the present invention, "functional food" is understood as a natural or processed food that contains known biologically-active compounds, such as beneficial microorganisms, which provide a health benefit, such as the prevention and/or treatment of diseases, in the particular case of the present invention, the treatment and/or prevention of infections of the oral cavity, such as caries.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient.

As used herein, an "oral health composition" means a composition which maintains and/or improves the health of the oral cavity, for example by preventing, reducing and/or eliminating infections in the oral cavity, including caries and periodontal disease.

During the description and the claims, the word "comprising" and its variants do not intend to exclude other technical characteristics, additives, components or steps. In addition, the term "comprising" may also encompass the term "consisting of".

Bacterial Strain of the Invention

The present invention relates to a new bacterial strain deposited at the Colección Española de Cultivos Tipo (CECT), which is located at Universidad de Valencia, Parc Cientific Universitat de València, Catedràtico Agustin Escardino, 9, 48980 Paterna (Valencia). The new bacterial strain was deposited by Servicio Galego de Saúde (SERGAS), with address on Edificio Administrativo San Lázaro, 15703, Santiago de Compostela, A Coruña, on Jul. 20, 2018, and was assigned the accession number CECT 9174. The reference assigned by the depositor is S8. From now on, this strain may be referred in the present document as the "bacterial strain of the present invention", CECT 9174.

The present invention further relates to a bacterial strain which genome has at least 95% average nucleotide identity (ANI, Richter M and Roselló-Mora R. 2009. PNAS 108: 19128-131), such as 95%, 98%, 97%, 98% or 99% with the DNA sequence of the whole genome of the bacterial strain of the present invention, CECT 9174.

The degree of identity between two sequences can be determined by conventional methods, for example, by means of standard sequence alignment algorithms known in the state of the art, such as, for example BLAST (Altschul S. F. et al. Basic local alignment search tool. J Mol Biol. 1990 Oct. 5; 215(3):403-10).

This bacterial strain with access number CECT 9174, was isolated from the oral cavity, in particular from the dental plaque of adult human subjects with low caries prevalence. The novel strain CECT 9174 has an antimicrobial effect, in particular against the cariogenic organism *S. mutans*. It has been demonstrated that the bacterial strain of the present invention, CECT 9174, is able to secrete to the extracellular media one or more substances with antimicrobial effect, in particular able to inhibit *S. mutans* growth, see, e.g., Example 4. In addition, the novel strain CECT 9174 has an antimicrobial effect against periodontopathogens, namely bacteria involved in the pathogenesis and development of periodontal disease, such as for example *Veillonella parvula, Aggregatibacter actinomycetemcomitans* and *Actinomyces naeslundii*.

The bacterial strain of the present invention has been shown to affect the development of a biofilm comprising *Streptococcus oralis, Veillonella parvula, Actinomyces naeslundii, Fusobacterium nucleatum, Aggregatibacter actinomycetemcomitans* and *Porphyromonas gingivalis*. In addition, the bacterial strain of the present invention has been shown to inhibit the development of a mature biofilm comprising *V. parvula, A. naeslundii, F. nucleatum, A. actinomycetemcomitans* and *P. gingivalis*. Accordingly, it has been shown that the bacterial strain of the present invention has a potent inhibitory effect against periodontal pathogens. The bacterial strain of the present invention is a useful agent in the prevention and treatment of the periodontal disease.

The bacterial strain of the present invention belongs to a new species, since it has an Average Nucleotide Identity (ANI) >10% with respect to all *Streptococcus* species sequenced (see Example 3) and has been classified along with *Streptococcus oralis* and *Streptococcus oligofermentans*. A taxonomic analysis of the 16S rRNA of CECT 9174 (the bacterial strain of the present invention) Indicated that this strain is closely related to *Streptococcus mitis* and some *Streptococcus* spp. oral clones. A taxonomic analysis of the 23S rRNA of CECT 9174 (the bacterial strain of the present invention) indicated that this strain is closely related to *Streptococcus dentisani* 7747 and *Streptococcus igurinus* (see Example 3).

The bacterial strain of the present invention is a coccus-shaped Gram positive microorganism, facultatively anaerobic, catalase-negative, which forms chains when growing. Phenotypically, it is classified as belonging to the *mitis/oralis* group (Ruoff K L. Miscellaneous Catalase-Negative, Gram-Positive Cocci: Emerging Opportunists. *Journal of Clinical Microbiology.* 2002; 40(4):1129-1133. doi:10.1128/JCM.40.4.1129-1133.2002; Facklam R. What Happened to the Streptococci: Overview of Taxonomic and Nomenclature Changes. *Clinical Microbiology Reviews.* 2002; 15(4): 613-630. doi:10.1128/CMR.15.4.613-630.2002) and genetically it is grouped according to the ANI value together with *Streptococcus oralis* and *Streptococcus oligofermentans*.

The present invention further relates to a biologically pure culture of a novel *Streptococcus* spp. strain, deposited at the Colección Española de Cultivos Tipo (CECT), by Servicio Galego de Saúde (SERGAS), with accession number CECT 9174 (the bacterial strain of the present invention), or a bacterial strain which genome has at least 95% average nucleotide identity, such as 95%, 96%, 97%, 98% or 99% with the DNA sequence of the whole genome of the bacterial strain of the present invention, CECT 9174.

Supernatant and Extract of the Present Invention

The present invention further provides an extract comprising the bacterial strain of the present invention, or a bacterial strain which genome has at least 95% average nucleotide identity, such as 95%, 96%, 97%, 98% or 99% with the DNA sequence of the whole genome of the bacterial strain of the present invention, CECT 9174.

The extract or crude extract of the present invention may be prepared by culturing the bacterial strain of the present invention, or a bacterial strain which genome has at least 95% average nucleotide identity, such as 95%, 96%, 97%, 98% or 99% with the DNA sequence of the whole genome of the bacterial strain of the present invention, CECT 9174, to reach a sufficient amount of cells (CFU/ml), such as, for example, $10^8$-$10^9$ CFU/ml, and homogenising the cellular fraction of the culture. As the skilled person would know, the cellular fraction may be obtained, for example, by centrifuging the culture and discarding the supernatant.

The skilled person is aware of homogenising techniques for bacteria. For example, the bacteria may be homogenised by using a lysis buffer which disrupts the cell wall.

The homogenate is the extract or crude extract according to the present invention.

The present invention further provides a supernatant derived from the cultivation of the bacterial strain of the present invention or a bacterial strain which genome has at least 95% average nucleotide identity, such as 95%, 96%, 97%, 98% or 99% with the DNA sequence of the whole genome of the bacterial strain of the present invention, CECT 9174.

The supernatant of the present invention may be prepared as follows. The bacterial strain of the present invention, or a bacterial strain which genome has at least 95% average nucleotide identity, such as 95%, 96%, 97%, 98% or 99% with the DNA sequence of the whole genome of the bacterial strain of the present invention, CECT 9174 is cultured in order to reach a sufficient amount of cells (CFU/ml), such as, for example, $10^8$-$10^9$ CFU/ml. Then, the culture is centrifuged and the supernatant is recovered and preferably filtered using, for example, a 0.22 µm filter. This way, the recovered supernatant is free from bacteria.

It has been demonstrated that the bacterial strain of the present invention, CECT 9174, is able to secrete to the extracellular media one or more substances with antimicrobial effect, in particular able to inhibit *S. mutans* growth (see, e.g., Example 4). Accordingly, the supernatant derived from the cultivation of the bacterial strain of the present invention, or a bacterial strain which genome has at least 95% average nucleotide identity, such as 95%, 98%, 97%, 98% or 99% with the DNA sequence of the whole genome of the bacterial strain of the present invention, CECT 9174 has bactericide activity, which is useful in the maintenance and/or improvement of the health status of the oral cavity.

Compositions, Probiotics and Medical Foods of the Invention

The present invention provides compositions comprising the bacterial strain of the present invention.

For Instance, the present invention provides a composition comprising the bacterial strain of the present invention, or a bacterial strain which genome has at least 95% average nucleotide identity, such as 95%, 98%, 97%, 98% or 99% with the DNA sequence of the whole genome of the bacterial strain of the present invention, CECT 9174, or culture, or extract, or supernatant of the present invention. The composition may be a pharmaceutical composition, an oral health composition, a probiotic, a medical food composition or a functional food.

The compositions of the present invention may further comprise other antimicrobial agents such as antibiotics or other antibacterial microorganisms.

The bacterial strain or culture of the present invention or a bacterial strain which genome has at least 95% average nucleotide identity, such as 95%, 96%, 97%, 98% or 99% with the DNA sequence of the whole genome of the bacterial strain of the present invention, CECT 9174, or culture, or extract, or supernatant may be comprised in a therapeutic formulation or pharmaceutical composition, which is a formulation or composition suitable for administration of the bacterial strain or culture of the present invention to a subject in need thereof, preferably a subject susceptible of suffering from oral infections such as caries and/or periodontal disease. In general, therapeutic formulations and pharmaceutical compositions according to the present invention comprise the bacterial strain or culture of the present invention and a pharmaceutically acceptable carrier, diluent and/or excipient.

As used herein, the expression "pharmaceutically acceptable carrier, diluent and/or excipient" means a vehicle, such as a non-toxic solvent, dispersant, excipient, adjuvant, or other material for delivery of the bacterial strain or culture of the present invention, which is compatible with bacterial cell viability or activity of the bacterial cells or culture. Suitable pharmaceutically acceptable carrier, diluent and/or excipient for use in the present invention are well known to those skilled in the art.

The bacterial strain of the present invention or a bacterial strain which genome has at least 95% average nucleotide identity, such as 95%, 98%, 97%, 98% or 99% with the DNA sequence of the whole genome of the bacterial strain of the present invention, CECT 9174, or culture, or extract, or supernatant of the present invention, can be formulated in many forms suitable for oral administration. For example, the bacterial strain or culture of the present invention or a bacterial strain which genome has at least 95% average nucleotide identity, such as 95%, 98%, 97%, 98% or 99% with the DNA sequence of the whole genome of the bacterial strain of the present invention, CECT 9174, or culture, or extract, or supernatant of the present invention can be directly administered to the oral cavity. For example, the bacterial strain of the present invention, or a bacterial strain which genome has at least 95% average nucleotide identity, such as 95%, 98%, 97%, 98% or 99% with the DNA sequence of the whole genome of the bacterial strain of the present invention, CECT 9174, or culture, or extract, or supernatant of the present invention can be applied to the oral cavity in the form of a spray. It can also be administered in the form of toothpaste, a mouthwash, a mouth rinse, gargle, capsule, syrup, chewing gum, lozenges, tablets, chewable tablets, etc.

The bacterial strain of the present invention or a bacterial strain which genome has at least 95% average nucleotide identity, such as 95%, 98%, 97%, 98% or 99% with the DNA sequence of the whole genome of the bacterial strain of the present invention, CECT 9174, or culture, or extract, or supernatant of the present invention may be comprised in an oral health composition, namely a composition suitable for oral administration which maintains and/or improves the health status of the oral cavity. Preferably, the oral health composition of the present invention is administered to a subject in need thereof, in particular a subject susceptible of suffering from infections caused by Gram negative and/or Gram positive bacteria, in particular by S. mutans, such as caries and/or infections caused by periodontal pathogens, such as periodontal disease. The oral health composition of the present invention may be formulated as a liquid, spray, of toothpaste, a mouthwash, a mouth rinse, gargle, syrup, etc. The oral health composition of the present invention may further comprise antimicrobial agents, antibacterial strains, anti-cariogenic agents such as xylitol or fluoride.

The bacterial strain of the present invention, or a bacterial strain which genome has at least 95% average nucleotide identity, such as 95%, 98%, 97%, 98% or 99% with the DNA sequence of the whole genome of the bacterial strain of the present invention, CECT 9174, or culture, or extract, or supernatant of the present invention may be used as probiotics. The probiotics of the present invention may be added to food such as dairy products (e.g., milk, yogurt), or may be consumed on their own, for example in the form of lozenges, tablets, capsules, powder, etc. They can also be added to dietary supplements.

The bacterial strain of the present invention, or a bacterial strain which genome has at least 95% average nucleotide identity, such as 95%, 98%, 97%, 98% or 99% with the DNA sequence of the whole genome of the bacterial strain of the present invention, CECT 9174, or culture, or extract, or supernatant of the present invention may be comprised in a medical food composition or a functional food.

Medical Uses of the Bacterial Strain of the Present Invention

The inventors of the present application have surprisingly found that the bacterial strain deposited at the Colección Española de Cultivos Tipo (CECT) by Servicio Galego de Saúde (SERGAS), on Jul. 20, 2018, with accession number CECT 9174 shows advantageous effects for the human health, in particular for the oral health. In addition, the inventors of the present application have found that the supernatant or medium derived from the culture of the bacterial strain of the present invention shows advantageous effects for the human health, in particular for the oral health. The bacterial strain of the present invention, CECT 9174, Is able to secrete to the extracellular media one or more substances with antimicrobial effect, in particular able to inhibit S. mutans growth (see, e.g., Example 4).

The bacterial strain of the present invention has been shown to have an antibacterial effect, in particular against S. mutans, which is one of the dental plaque-inhabiting streptococcal species, considered to be one of the principal causative agents of oral infections, in particular caries.

In addition, the bacterial strain of the present invention has been shown to have an antibacterial activity against periodontal pathogens, such as *A. naeslundii, V. parvula* and *A. actinomycetemcomitans*. In addition, the bacterial strain of the present invention has been shown to affect the development of a biofilm comprising *Streptococcus oralis, Veillonella parvula, Actinomyces naeslundii, Fusobacterium nucleatum, Aggregatibacter actinomycetemcomitans* and *Porphyromonas gingivalis*. In addition, the bacterial strain of the present invention has been shown to inhibit the development of a mature biofilm comprising *V. parvula, A. naeslundii, F. nucleatum, A. actinomycetemcomitans* and *P. gingivalis*. Accordingly, it has been shown that the bacterial strain of the present invention has a potent inhibitory effect against periodontal pathogens. The bacterial strain of the present invention is a useful agent in the prevention and treatment of the periodontal disease.

Accordingly, the present invention further provides the bacterial strain of the present invention, or a bacterial strain which genome has at least 95% average nucleotide identity, such as 95%, 98%. 97%, 98% or 99% with the DNA sequence of the whole genome of the bacterial strain of the present invention, CECT 9174, or culture, or extract, or supernatant, or composition (pharmaceutical composition, oral health composition, medical food composition), or probiotic, or functional food of the present invention for use as a medicament, preferably an anti-microbial medicament, in particular against infections caused by Gram positive and/or Gram negative bacteria, more particularly against *S. mutans* and/or against periodontal pathogens.

The present invention further provides the bacterial strain of the present invention, or a bacterial strain which genome has at least 95% average nucleotide identity, such as 95%, 98%, 97%, 98% or 99% with the DNA sequence of the whole genome of the bacterial strain of the present invention, CECT 9174, or culture, or extract, or supernatant, or composition (pharmaceutical composition, oral health composition, medical food composition), or probiotic, or functional food of the present invention for use in the prophylactic or therapeutic treatment of infectious diseases of the oral cavity, preferably infections caused by Gram positive and/or Gram negative bacteria, in particular by *S. mutans* and/or infections caused by periodontal pathogens, more preferably caries and/or periodontal disease. Accordingly, the present invention provides a method for the prevention and/or treatment of infectious diseases of the oral cavity, preferably infections caused by Gram positive and/or Gram negative bacteria, in particular by *S. mutans* and/or infections caused by periodontal pathogens, more preferably caries and/or periodontal disease, which comprises, or alternatively, consist of, administering to a subject in need thereof a therapeutically effective amount of the bacterial strain of the present invention, or a bacterial strain which genome has at least 95% average nucleotide identity, such as 95%, 98%, 97%, 98% or 99% with the DNA sequence of the whole genome of the bacterial strain of the present invention, CECT 9174, or culture, or extract, or supernatant, or composition (pharmaceutical composition, oral health composition, medical food composition), or probiotic, or functional food of the present invention.

The present invention further provides the use of the bacterial strain of the present invention, or a bacterial strain which genome has at least 95% average nucleotide identity, such as 95%, 98%, 97%, 98% or 99% with the DNA sequence of the whole genome of the bacterial strain of the present invention, CECT 9174, or culture, or extract, or supernatant, or composition (pharmaceutical composition, oral health composition, medical food composition), or probiotic, or functional food of the present invention to maintain and/or improve oral health. For instance, the present invention provides the use of the bacterial strain of the present invention, or a bacterial strain which genome has at least 95% average nucleotide identity, such as 95%, 98%, 97%, 98% or 99% with the DNA sequence of the whole genome of the bacterial strain of the present invention, CECT 9174, or culture, or extract, or supernatant, or composition (pharmaceutical composition, oral health composition, medical food composition), or probiotic, or functional food of the present invention to prevent the development of oral infections, such as caries and/or periodontal disease, or to reduce or eliminate the presence of oral infections.

For those experts in the state of the art, other objects, advantages and characteristics of the invention are released in the section of the description and practice of the invention. The following examples and drawings are provided as illustrations, and are not intended to limit the present invention.

EXAMPLES

Example 1

Isolation and Characterization of the New Bacterial Strain (the Bacterial Strain of the Present Invention, Deposited at the Colección Española De Cultivos Tipo (CECT), by Servicio Galego De Saúde (SERGAS), with Address on Edificio Administrativo San Lázaro, 15703, Santiago De Compostela, a Coruña, on Jul. 20, 2016, with Accession Number CECT 9174).

The present invention provides a specific bacterial strain which presents inhibitory activity against the cariogenic microorganism *S. mutans*.

Materials and Methods

Bacterial Strains and Culture Conditions

Samples of the supragingival dental plaque and saliva of patients selected were taken. The samples were transported in Amies medium swab (Copan Diagnostics Inc.) for transport to the laboratory of Microbiology Service of University Hospital of Vigo (Spain). Upon arrival they were planted by exhaustion on agar plates (Biomerieux): chocolate (CH), blood agar (AS), agar nalidixic colistin-acid (CNA) selective for Gram-positive and MacConkey agar (MCK) selective for Gram-negative.

Samples were incubated under the following conditions: CH, AS and CNA in aerobically with 5% $CO_2$ and MCK in aerobic atmosphere, at 35-37° C. for 24 hrs.

After the incubation period colonies were selected to study based on colonial morphology (size, shape and pigmentation of colonies). Cell morphology was selected mainly with α-hemolytic *Streptococcus* suspected of belonging to the *viridans* group. To obtain pure cultures, different isolates were subcultured on chocolate agar plates and incubated aerobically with $CO_2$ at 5% to 35-37° C. for 24 hrs.

Biochemical analysis and sugar fermentation characteristics of the isolates were determined by API®20 API®50 Strept and CHL (bioMérieux) systems according to the manufacturer's instructions. Positivity and negativity of biochemical test was evaluated according to the colour code specified in the API system.

Todd-Hewitt medium supplemented with 5% yeast extract and 5% of foetal bovine serum (THY) was used for the growth curve and inhibition in liquid medium.

Growth Inhibition Assay on a Lawn Culture of *S. mutans*

0.3 McFarland suspension of *S. mutans* CECT 479 was performed in brain-heart infusion (BHI) plates (Conda) to obtain a growth mode tapestry. CECT 9174 was deposited as a 10 uL button, after growth on chocolate agar for 24 hours. S. oral/s CECT 907T was used as a negative control and S. dentisani CECT 8312 and S. dentisani 8313 were used as positive controls. The plates were incubated in 5% $CO_2$ atmosphere. After 48 hours the presence of inhibition zones produced by each is evaluated.

Growth Inhibition Assay on Mixed Cultures

Two or three colony forming units (CFU) of CECT 9174 of a pure plate culture in CH medium (Biomerieux) were inoculated into 10 ml of broth THY in 50 ml tubes (BD Falcon) and incubated in a shaker oven at 35° C. and 100 rpm. Inoculum size for the mixed culture was adjusted by reading OD600 In a spectrometer (Unicam Heλios ß), so that the number of colony forming units (CFU) in the mixed culture of S. mutans and each isolated study reached the $10^8$ CFU/mL range. To determine the inoculum size, serial dilutions in plates were performed in CH medium, as described below.

The mixed culture was performed by incubating 100 µL of each microorganism inoculum after adjustment according to OD600 in fresh THY 10 ml medium in a 50 ml tube. The final concentration in the mixed culture was $10^5$ CFU/mL. After incubation stirring during 24 hours in an oven at 35° C. and 100 rpm, the resulting number of CFUs was determined by serial dilutions ($10^{-2}$, $10^{-3}$, $10^{-4}$, $10^{-5}$, $10^{-6}$, $10^{-7}$) in THY, Inoculating 100 µL of each dilution in CH and stretching the inoculum with an inoculation loop Drigalski. In order to know the number of CFUs resulting from independent culture of each of streptococci present in the mixed culture, they were each incubated independently at a concentration of $10^5$ CFU/mL, during 24 hours in a shaker oven at 35° C. and 100 rpm. The determination of the resulting number of CFU was performed as described above, by serial dilutions in CH plates. All tests were performed in 3 different replica in order to ensure the reproducibility of the results.

Results and Discussion

Isolation of CECT 9174

The CECT 9174 isolate was obtained in dental plaque samples from a group of volunteers who attended the Special Care Dentistry Unit at the University of Santiago de Compostela (Spain). Patients with good oral health were selected without evidence of tooth decay among a low caries prevalence population. The oral health status was evaluated by a dentist following the World Health Organization (WHO) recommendations and nomenclature of Studies on Oral Health.

Growth Inhibition Assay: "Spot-On-the-Lawn" Test

The study of the activity of the novel Streptococcus spp. strain to inhibit the growth of S. mutans in vitro was performed by the method of "spot-on-the-lawn" on the solid culture BHI, tested under two atmosphere conditions (anaerobiosis or 5% $CO_2$ atmosphere). A positive result was defined as the presence of a halo of growth inhibition (sensitive strain).

Figure 1:
FIG. 1. Growth inhibition area for CECT 9174 on the plates inoculated with *S. mutans* of the BHI agar.

FIG. 1 shows the inhibition halo produced by CECT 9174 on a lawn culture of S. mutans. The results show a halo of growth inhibition of S. mutans in the presence of CECT 9174.

Growth Inhibition Assay: Mixed Cultures in Liquid Medium

The present assay was performed as described above under "Growth Inhibition assay on mixed cultures".

Figure 2:
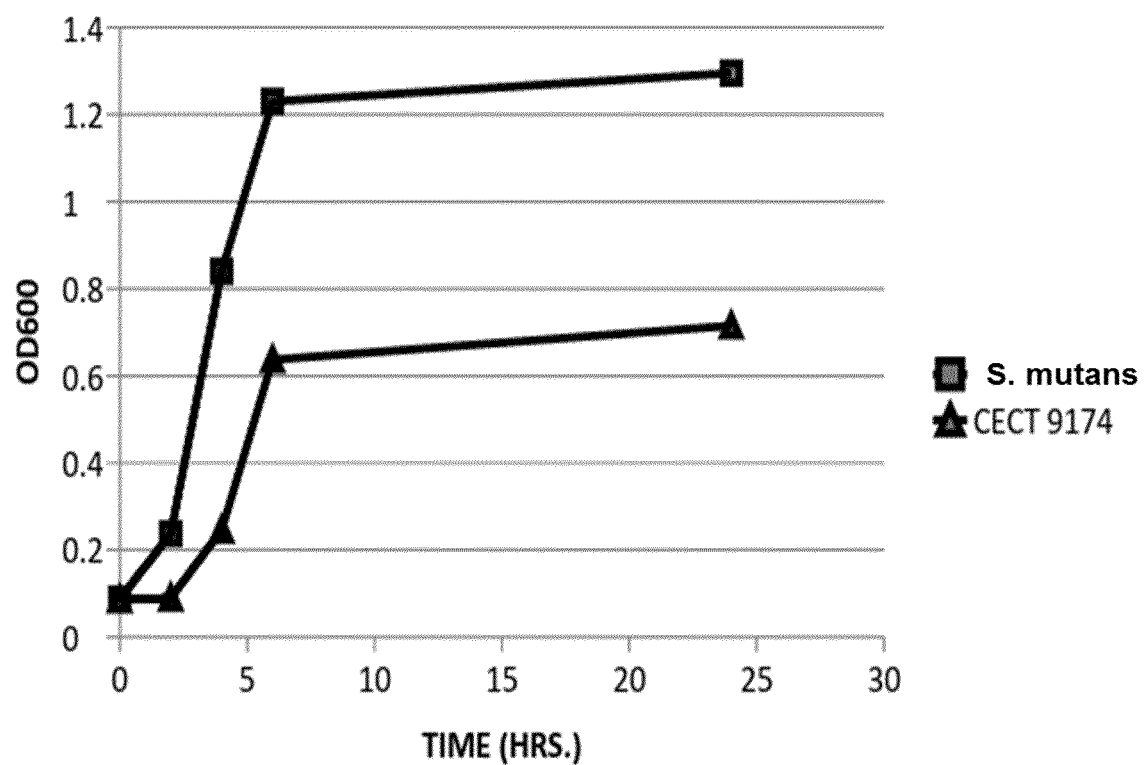
FIG. 2. Growth curve of *S. mutans* and CECT 9174 (OD600 average, six replicates tested) in THY liquid medium.

It has been shown that the growth capacity in liquid medium is much higher for S. mutans than for CECT 9174 (the bacterial strain of the present invention), as illustrated in their growth curves in FIG. 2.

Both Isolates (S. mutans and CECT 9174 (the bacterial strain of the present invention)) were combined in liquid medium at the same concentration ($\approx 10^6$ CFU/mL) and the growth in CFU/mL was observed after 24 h of incubation.

Figure 3:
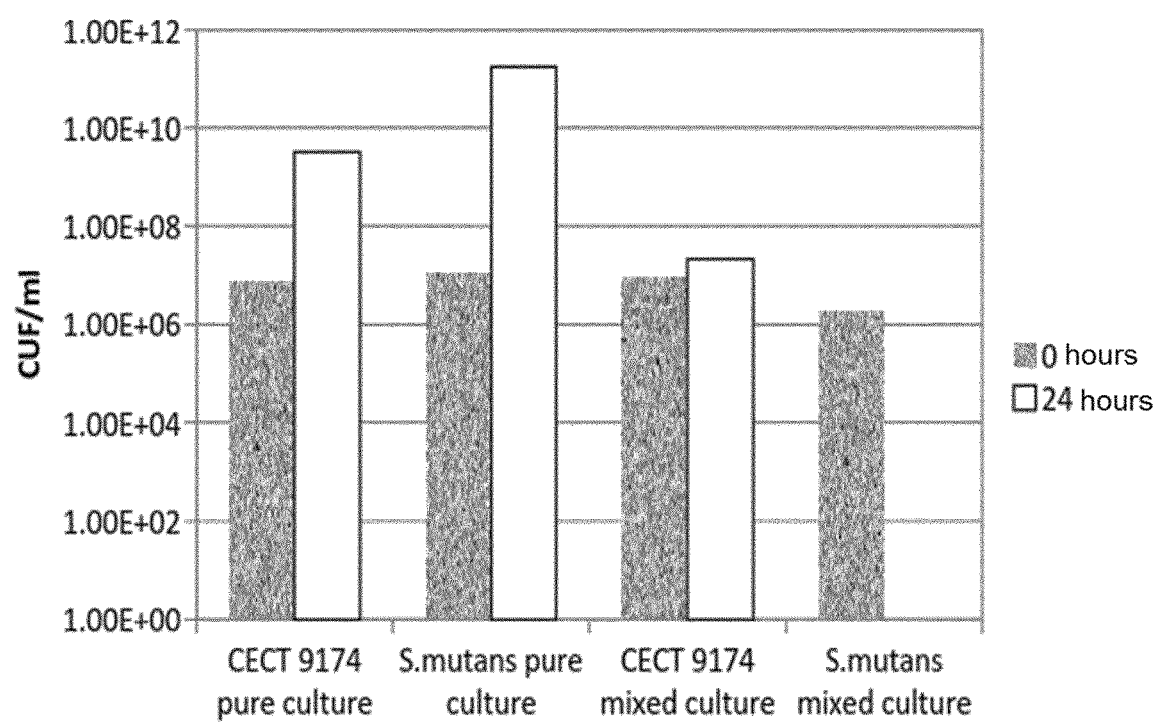
FIG. 3. CECT 9174 and *S. mutans* growth difference in pure liquid medium and coculture in THY culture after 24 hours incubation at 5% $CO_2$ atmosphere.

The amount of CECT 9174 was increased after 24 h, whereas the amount of S. mutans stops growing in the mixed culture, even if this microorganism showed a higher growth rate in liquid culture (FIG. 3).

Example 2

Evaluation of the Ability of the Novel Streptococcus Spp. to Inhibit Bacterial Growth of Other Bacterial Species in an in Vitro Biofilm Model The aim of this study was to evaluate the antibacterial activity of a novel Streptococcus spp. strain (the strain of the present invention) against bacteria involved in the development of an in vitro oral biofilm model.

Materials and Methods

Bacterial Strains and Culture Conditions

Standard reference strains of Streptococcus oralis CECT 907T, Veillonella parvula NCTC 11810, Actinomyces naeslundii ATCC 19039, Fusobacterium nucleatum DMSZ 20482, Aggregatibacter actinomycetemcomitans DSMZ 8324 and Porphyromonas gingivalis ATCC 33277 were used.

Bacteria were grown on blood agar plates (Blood Agar Oxoid No 2; Oxoid, Basingstoke, UK), supplemented with 5% (v/v) sterile horse blood (Oxoid), 5.0 mg $mL^{-1}$ hemin (Sigma, St. Louis, Mo., USA) and 1.0 mg $mL^{-1}$ menadione (Merck, Darmstadt, Germany) in anaerobic conditions (10% $H_2$, 10% $CO_2$, and balance $N_2$) at 37° C. for 72 h. The novel Streptococcus spp. strain was grown in the same conditions described above.

Growth Inhibition Assay in Pure Cultures of the Six Standard Reference Strains Promoted by the Antimicrobial Activity of the Novel Streptococcus Spp. Strain Inoculums from each one of the six reference strains and the novel Streptococcus spp. were grown in anaerobic conditions (10% $H_2$, 10% $CO_2$, and balance $N_2$) at 37° C. for 24 h in modified BHI medium, a protein-rich medium containing brain-heart infusion (BHI) (Becton, Dickinson and Company, Franklin Lakes, N.J., USA) supplemented with 2.5 g $L^{-1}$ mucin (Oxoid), 1.0 g $L^{-1}$ yeast extract (Oxoid), 0.1 g $L^{-1}$ cysteine (Sigma), 2.0 g $L^{-1}$ sodium bicarbonate (Merck), 5.0 mg $mL^{-1}$ hemin (Sigma), 1.0 mg $mL^{-1}$ menadione (Merck) and 0.25% (v/v) glutamic acid (Sigma).

The bacterial growth was harvested at last-exponential phase (measured by spectrophotometry). The inhibition assay was performed by the method of "spot-on-the-lawn" on two solid culture mediums. The six reference strains were inoculated on Blood Agar plates and BHI plates, with a swab, rubbing it on its surfaces in order to ensure a good distribution of the inoculum on the surface of the medium. Then, the novel Streptococcus spp. was placed onto the inoculated surfaces of the agar as a button, by collecting a loopful of a fresh culture of strain on blood agar plates.

Plates were incubated in both, anaerobic conditions (10% $H_2$, 10% $CO_2$, and balance $N_2$) and at 5% $CO_2$ atmosphere (5% $CO_2$, 20.07% $O_2$,) at 37° C. for 98 h. After incubation, the diameter of the growth inhibition zones around the novel Streptococcus spp. was measured.

In Vitro Inhibition Assay of Biofilm Development Promoted by the Novel Streptococcus Spp. Strain Biofilms were generated using the method described by Sánchez and co-workers (Sánchez M C, Llama-Palacios A, Blanc V, León R, Herrera D, Sanz M; "Structure, viability and bacterial kinetics of an in vitro biofilm model using six bacteria from the subgingival microbiota", *J Period Res*, 2011 April; 48(2):252-80) with slightly different bacterial concentrations when preparing the bacterial suspension. Briefly, planktonic cultures of the six reference strains and the novel *Streptococcus* spp. strain were grown anaerobically in supplemented BHI medium, described above. Upon reaching mid-exponential phase (measured by spectrophotometry), a mixed bacteria suspension in modified BHI medium containing $10^3$ colony forming units (CFU) $mL^{-1}$ for *S. oralis* and/or novel *Streptococcus* spp. strain, $10^5$ CFU $mL^{-1}$ for *V. parvula* and *A. naeslundii*, and 107 CFU $mL^{-1}$ for *F. nucleatum, A. actinomycetemcomitans* and *P. gingivalis* was prepared. Then, sterile calcium hydroxyapatite (HA) disks of 7 mm of diameter and 1.8 mm (standard deviation, SD=0.2) of thickness (Clarkson Chromatography Products, Williamsport, Pa., USA) were placed in the wells of a 24-well tissue culture plate (Greiner Bio-one, Frickenhausen, Germany). Each well was inoculated with 1.5 mL mixed bacteria suspension prepared and incubated in anaerobic conditions (10% $H_2$, 10% $CO_2$, and balance $N_2$) at 37° C. for 72 h. The plates employed for assessing the sterility of the culture medium were used as controls.

Three Independent bacterial suspensions were prepared, containing, respectively:
(1) *S. oralis, V. parvula, A. naeslundii, F. nucleatum, A. actinomycetemcomitans* and *P. gingivalis;*
(2) The novel *Streptococcus* spp. strain (CECT 9174), *S. oralis, V. parvula, A. naeslundii, F. nucleatum, A. actinomycetemcomitans* and *P. gingivalis;*
(3) The novel *Streptococcus* spp (CECT 9174), *V. parvula, A. naeslundii, F. nucleatum, A. actinomycetemcomitans* and *P. gingivalis.*

Scanning Electron Microscopy (SEM) Analysis

Before SEM analysis, disks covered with biofilms grown in vitro for 72 h were fixed in 4% paraformaldehyde and 2.5% glutaraldehyde for 4 h at 4° C. Then, the disks were washed once in PBS and once in sterile water (immersion time per wash 10 min) and dehydrated through a series of graded ethanol solutions (50, 60, 70, 80, 90 and 100%; immersion time per series 10 min). Then, the samples were critical point dried, sputter-coated with gold and analyzed by electron microscopy JSM 6400 (JSM6400; JEOL, Tokyo, Japan) with a back-scattered electron detector and an image resolution of 25 KV. Analyses were carried out at ICTS National Centre of Electronic Microscopy (Campus de Excelencia Internacional de Moncloa, Universidad Complutense de Madrid, Spain).

Results and Discussion

Growth Inhibition Assay

The study of the activity of the novel *Streptococcus* spp. strain to inhibit the growth of the six reference strains involved in the formation of an oral biofilm in vitro was performed by the method of "spot-on-the-lawn" on two solid cultures, BHI and a supplemented Blood agar, tested under two atmosphere conditions (anaerobiosis or 5% $CO_2$ atmosphere). A positive result was defined as the presence of a halo of growth inhibition (sensitive strain).

Figure 4:
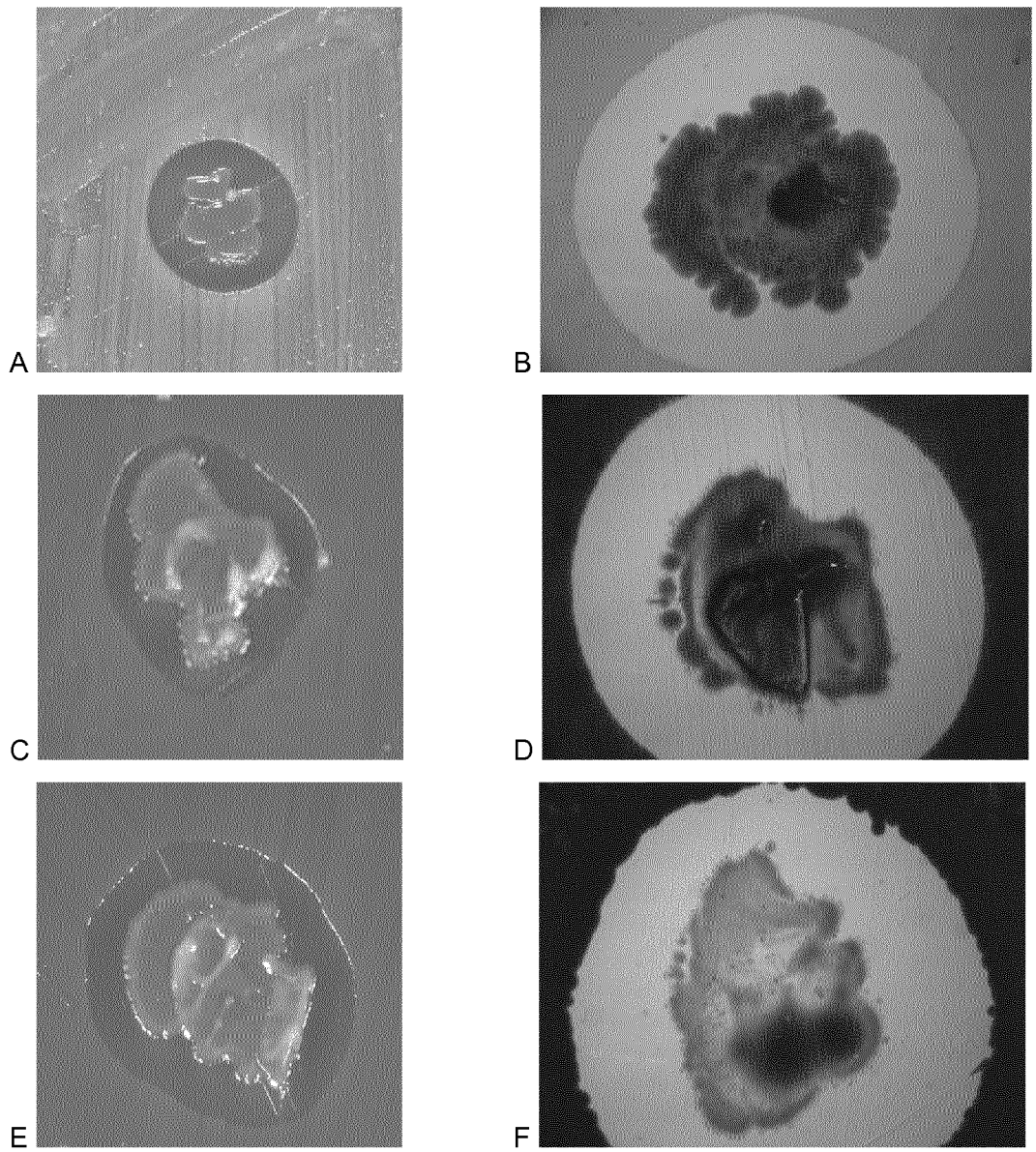
FIG. 4. Micrographs obtained with a Leica magnifying lenses, objective 1×, at 5% $CO_2$ atmosphere for 98 h, of the co-culture of novel *Streptococcus* spp. strain (CECT 9174), Inoculated on surfaces of the BHI agar as a button and: A,B) *Actinomyces naeslundii*, C,D) *Veillonella parvula*, E,F) *Aggregatibacter actinomycetemcomitans*, Inoculated on the plates with a swab, rubbing it on its surfaces in order to ensure a good distribution of the inocula. Growth inhibition areas around the novel *Streptococcus* spp. strain (CECT 9174) can be observed for *A. naeslundii*, *V. parvula* and *A. actinomycetemcomitans*.

Results on growth inhibition are detailed in Table 1. The novel *Streptococcus* spp. strain clearly inhibited the growth of *A. naeslundii, V. parvula* and *A. actinomycetemcomitans* under an atmosphere of 5% $CO_2$ and using BHI as culture medium (FIG. 4). No antibacterial activity was observed for these bacterial species in the others circumstances studied. For *S. oralis, F. nucleatum* and *P. gingivalis* no antibacterial activity was observed in any of the studied scenarios.

Scanning Electron Microscopy Analysis

Figure 5:
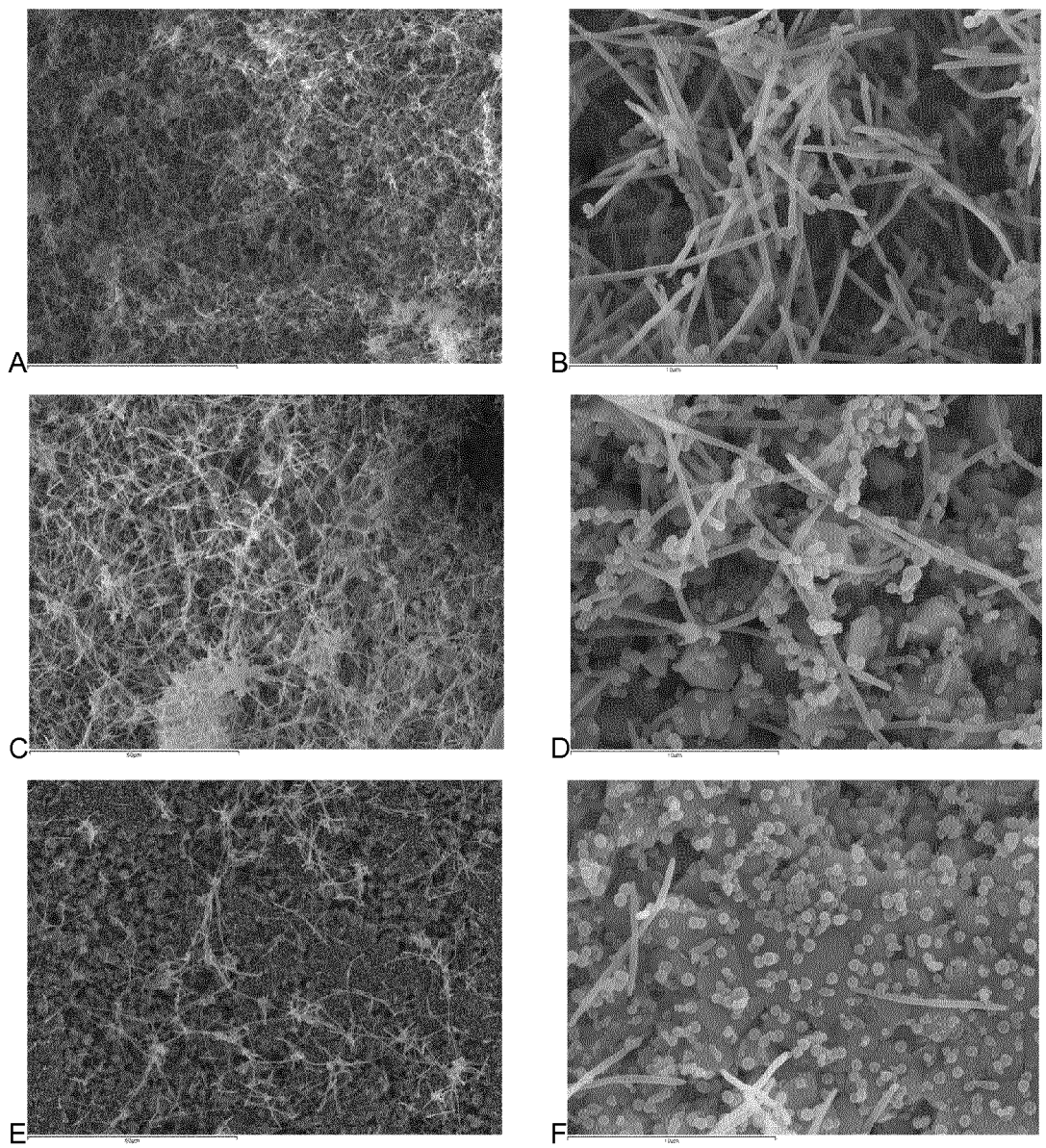
FIG. 5. Scanning electron microscopy (SEM) of oral biofilms formed in vitro on hydroxyapatite disks. Biofilms, formed after 72 h of incubation, were composed of: (A,B) *Streptococcus oralis*, *Veillonella parvula*, *Actinomyces naeslundii*, *Fusobacterium nucleatum*, *Aggregatibacter actinomycetemcomitans* and *Porphyromonas gingivalis*; (C,D) the novel *Streptococcus* spp. strain plus *Streptococcus oralis*, *Veillonella parvula*, *Actinomyces naeslundii*, *Fusobacterium nucleatum*, *Aggregatibacter actinomycetemcomi*-

Additional evaluation of the antibacterial activity of novel *Streptococcus* spp. strain against bacterial species involved in the development of an oral in vitro biofilm in anaerobic conditions was conducted via Scanning Electron Microscopy (SEM), indicating that this bacterium produced an important effect In the biofilm formation under the conditions used, specifically inhibiting its development, as can be seen in FIG. 5 (A-F).

Three different combinations of bacterium were tested:
(1) When biofilms contained the six bacterial species conventionally used in the biofilm model (*S. oralis, V. parvula, A. naeslundii, F. nucleatum, A. actinomycetemcomitans* and *P. gingivalis*), bacteria developed a well-structured bacterial community. Spindle-shaped rods, suggestive of *F. nucleatum* could be recognized, which seems to plays an important role maintaining the scaffold of the biofilm (FIGS. 5A and 5B).
(2) When the novel *Streptococcus* spp. strain (CECT 9174) was added together with the six standard reference strains (novel *Streptococcus* spp. Strain (CECT 9174) plus *S. oralis, V. parvula, A. naeslundii, F. nucleatum, A. actinomycetemcomitans* and *P. gingivalis*), the structure presented a lower density (FIGS. 5C and 5D), but without relevant differences when compared with the structure of the reference biofilm (FIGS. 5A and 5B). Along the biofilm, HA material is observed under the biomass (FIG. 5D), as irregular blocks. This finding was not observed in the reference biofilm for its higher density (FIG. 5B); therefore, it can be speculated that the presence of the new *Streptococcus* spp. strain (CECT 9174) affects the development of biofilm.
(3) When the novel *Streptococcus* spp. strain (CECT 9174) was added together with five of the standard reference strains (*V. parvula, A. naeslundii, F. nucleatum, A. actinomycetemcomitans* and *P. gingivalis*), excluding *Streptococcus oralis*, it could be observed a notorious inhibition of the development of a mature biofilm (FIGS. 5E and 5F). Bacteria appeared sparsely attached to the HA surface. Bacterial cells were arranged either as short streptococcal chains, isolated cells or as poor multicellular aggregates. Bacterial cells were disposed on the surface without the typical structure of the biofilm, with less presence of bacteria cells compared to the reference biofilm. Also, it could be observed that the predominant bacterial-species over the HA surface was the novel *Streptococcus* spp. strain (CECT 9174).

TABLE 1

Growth inhibition assay of the six bacterial reference strains implicated in the formation of the in vitro biofilm promoted by the novel *Streptococcus* spp. strain (CECT 9174). A positive result is considered when a halo of inhibition growth is observed (sensitive strain).

| Atmosphere | Culture Medium | Bacteria as a button | Bacteria rubbed on the plates surfaces. Presence of a halo of inhibition growth | | | | | |
|---|---|---|---|---|---|---|---|---|
| | | | So | An | Vp | Fn | Aa | Pg |
| 5% $CO_2$ | BHI | CECT 9174 | − | + | + | − | + | − |
| | Blood Agar | CECT 9174 | − | − | − | − | − | − |
| Anaerobic | BHI | CECT 9174 | − | − | − | − | − | − |
| | Blood Agar | CECT 9174 | − | − | − | − | − | − |

So: *Streptococcus oralis*; An: *Actinomyces naeslundii*, Vp: *Veillonella parvula*; Fn: *Fusobacterium nucleatum*; Aa: *Aggregatibacter actinomycetemcomitans*; Pg: *Porphyromonas gingivalis*.

Example 3

Comparison Between the Genome of CECT 9174, and the Rest of the Members of Streptococcus Genus which had been Sequenced Up to March 2015

The present example is aimed at sequencing and comparing the genome of a novel bacteria of the genus Streptococcus (the bacterial strain of the present invention, with accession number CECT 9174) with respect to all the known and annotated bacteria of the genus Streptococcus which will be performed by means of the JSpecies program by calculating the ANI indicator for bacteria annotated in databases.

A genomic DNA sample of the bacterial strain, which is designated by the internal code as indicated in the table listing the quality measurements of the sample after trimming (half of the initial sample, 141938, is trimmed by means of Roche High Pure kit in an attempt to improve the A260/230 ratio).

TABLE 2

The quality-to-amount ratio of sample 141936 which was designated as 141936A after trimming

| Internal code | Further ref. | ng/µl | A260/280 | A260/230 | total ng |
|---|---|---|---|---|---|
| 141936A | 1A-S6 | 19.2 | 1.85 | 1.70 | 597 |

Sample 141936A was then quantified fluorometrically using Qubit dsDNA BR Assay Kit (Life Technologies, Carlsbad, Calif., USA), giving a result of 8.5 ng/µl. By using this quantification as reference, the Nextera XT DNA Sample Preparation protocol was started with 250 pg of total DNA for library development. FIG. 6 shows the profile of Agilent 2100 Bioanalyzer (Agilent Technologies; Palo Alto, Calif.) for the Nextera library that has been obtained.

The quantification of the library that was obtained through the profile indicated in the preceding figure and that pertains to the library display in an Agilent Bioanalyzer, this library was at a concentration of 18.2 nM, with fragments having around 564 bp in average. Based on this quantification, the library was diluted at 4 nM for 300PE sequencing in Illumina MiSeq (Illumina Inc., San Diego, Calif., USA).

Sequencing and Quality Processing of Sequences

The library is loaded into Illumina MiSeq sequencer and 300PE sequencing is performed therein, as indicated above, and more than 1 Gb of total sequence information was obtained. Sequencing results in terms of the number of reads, average length and average quality of the reads obtained in the sequencer are shown in Table 3.

TABLE 3

Sequencing results of the samples for DNAseq experiment of the CECT 9174 (No. of sequences: number of sequences; Av. length: average length; Total sequenced: total amount of sequences obtained; Av. quality: average quality).

| Internal code | Further ref. | Direction | No. of sequences | Av. length (nts) | Total sequenced (Mb) | Av. quality |
|---|---|---|---|---|---|---|
| 141936A | 1A S6 | R1 | 4,829,330 | 217.00 | 1,051.00 | 35.81 |
|  |  | R2 | 4,829,330 | 219.00 | 1,060.00 | 33.18 |

Like in all Illumina paired-end sequencing, the sequences read in the R2 (reverse) direction usually have a lower average quality.

Files containing the sequences for each of the directions for our test sample were trimmed of adapters and filtered by quality, eliminating files that are of lower quality Q20 and Illumina adapters for NexteraDNAseq libraries.

This processing was performed using the cutadapt program, version v1.4, (http://code.google.com/p/cutadapt/). The result of the trimmed sequences, the average length and the average quality of said sequences are also shown in Table 4.

TABLE 4

Results of the sequences after filtering the DNAseq experiment by quality. (No. of sequences: number of sequences; Av. length: average length; Total sequenced: total amount of sequences obtained; Av. quality: average quality).

| Internal code | Further ref. | Direction | No. of sequences | Av. length (nts) | Total sequenced (Mb) | Av. quality |
|---|---|---|---|---|---|---|
| 141936A | 1A S6 | R1 | 4,683,023 | 184.00 | 865.00 | 36.13 |
|  |  | R2 | 4,683,023 | 205.00 | 963.00 | 36.11 |

The rest of the bioinformatics analysis was performed with the trimmed sequences.

Bioinformatics Analysis

Sequence Quality Control

The raw and trimmed sequences were examined with the FastQC program, version 0.10.1, (http://www.bioinformatics.babraham.ac.uk/projects/fastqc/), the quality result can be seen in the following figures showing an example of quality control.

FIG. 7 shows that the qualities of the sequenced bases of all the raw and trimmed sequences, after the adapter trimming. The average quality of the readings improves after the elimination of low-quality sequences, but in general, the values that we are seeing indicate a high quality sequencing process, and particularly a highly reliable subsequent bioinformatics analyses conducted on these sequences. This quality is higher than Q30, which Is the value used as a reference for the sequences obtained in projects with Illumina platforms, except at the final ends of sequencing, where the quality drops, and the lower quality of the R2 end can also be seen. Panels A and B of the figures on the right side show before and after the elimination of quality sequences and adapters, respectively. Other ways of depicting the average quality are shown in FIGS. 8 and 9.

FIG. 8 shows that the average quality of the sequenced bases is close to Q35 before adapter and quality trimming, Increasing the number of sequences within that average quality (distribution Is carried out once trimming has been performed). There is no indetermination in any case, as shown in FIG. 9.

GC content distribution in the raw and "trimmed" data Is superimposed on the theoretical distribution, so GC content bias during sequencing would not pose a problem, although there are indeed more sequences having a specific % of G+C content than what was expected. This data, together with sequence quality results, lead us to the next level of analysis.

Assembly

Adapter- and quality-trimmed sequences were assembled by means of the Abyss program (http://www.bcgsc.ca/platform/bioinfo/software/abyss), using the default options and only optimizing K-mer which provides the best assembly, i.e., that assembly which gives a smaller number of contigs, a greater number of long contigs (>500 nts) and where the length of the longest contig of the assembly is maximized. These results are summarized in Table 5.

TABLE 5

Results of the assemblies with different k-mers (total contigs: total number of contigs; median: median of contig length; N50: N50 of contig length; >500: number of contigs with more than 500 nts; median >500: median of the length of the number of contigs with more than 500 nts; max. length: longest contig)

| Kmer | total contigs | median | N50 | >500 | median >500 | max. length |
|---|---|---|---|---|---|---|
| kmer49 | 285 | 86 | 86 | 18 | 44963 | 546746 |
| kmer53 | 243 | 195 | 95 | 18 | 44983 | 546297 |
| kmer57 | 216 | 102 | 102 | 15 | 45003 | 680805 |
| kmer61 | 186 | 110 | 110 | 15 | 45023 | 680419 |
| kmer63 | 170 | 111 | 114 | 14 | 54575 | 680509 |
| kmer64 | 166 | 116 | 116 | 14 | 54454 | 679929 |

Based on the results of assembly statistics, it can be concluded that the assembly with kmer 63 Is the optimal assembly for use in the rest of the analysis.

Ten contigs are obtained, of which the largest one has 118,268 kb. Based on the contigs, the genome has a size of 1,916,980 nt and a GC percentage of 41.13%.

Annotation

Using the contigs obtained with the default parameters and Kmer 63, the open reading frames (ORFs) were predicted using the GLIMMER program, version 3.02 (https://ccb.jhu.edu/software/glimmer/). GLIMMER is the most widely used program for performing microorganism genome assembly searches (gene prediction). Likewise, RNAmmer, version 1.2, was used for rRNA prediction and tRNAscan tool, version 1.21, was used for tRNA prediction.

The identified ORFs were associated with a specific protein, and functionally annotated by means of associating each ORF with its related GO terms using BLAST2GO (https://www.blast2go.com/).

Once the ORFs have been annotated and taking into account the location of the rRNAs and tRNAs, a GFF file is constructed so that it can be used in the future for RNAseq experiments.

Classification by Means of ANI

With the annotated genome of the species under study, referred to as CECT 9174, said species can be classified by means of calculating the Average Nucleotide Identity (ANI). JSpecies program, version 1.2.1, (http://imedea.uib-csic.es/jspecies/) was used to allow carrying out this analysis.

The steps to follow were the introduction of the annotated genome of the species under study (CECT 9174) and the subsequent selection of the genus (in this case, *Streptococcus*) based on which all the sequenced and annotated bacteria were chosen for calculating the ANI.

According to the classification, taking into account the topology that we have identified by means of using the JSpecies program, the test species is classified together with *Streptococcus oralis* and *Streptococcus oligofermentans*.

FIG. 11 depicts the classification of the bacterium taking Into account the ANI.

Classification by Means of the Phylogeny of 18n rRNA and 238 rRNA

Since the organism's genome is at hand and the rRNAs contained therein have been predicted, we have decided to construct the phylogeny using these two regions of the genome, which are the most commonly used regions for microorganism classification. The steps followed in the analysis are described in the pipeline http://www.phylogeny.fr/documentation.cgi. Briefly, we aligned the sequences with MUSCLE 3.8.31, and subsequently used the Gblocks 0.91.b program to refine the alignment. With the refined alignment, we started constructing the phylogenetic tree using the phyML program, version 3.1. With the most plausible phylogenetic tree, we used the ape program (http://cran.r-project.org/web/packages/ape/ape.pdf) of statistical package R to draw the tree. All the 16 s and 23 s rRNAs pertaining to the *Streptococcus* genus from the SILVA database were chosen to allow carrying out the alignment, and the sequence of the sample under study was added to those sequences.

If we take into account the 18 s rRNA-based sequence, the strain under study is close to *Streptococcus mitis* and to some *Streptococcus* spp. oral clone.

According to the classification based on 23 s rRNA, the species under study, CECT 9174, is close to *Streptococcus dentisani* 7747 and *Streptococcus igurinus*.

Example 4

Plate Competition Assay

5 μL of CECT 9174 at a concentration of 1 McFarland were inoculated in BHI (adequate nutrition conditions) and BHI ‰ (nutritional restriction conditions) plates, and were incubated at 37° C. In $CO_2$ 5% atmosphere for 18 hours. Then, at a distance of 3-5 mm from the CECT 9174 colony, 5 μL of *S. mutans* 479 at a concentration of 1 McFarland were inoculated, and the plates were again incubated at 37° C. in de $CO_2$ 5% atmosphere for further 32 hours. Afterwards, *S. mutans* was only able to grow in a small portion far away from CECT 9174. This fact is enhanced in nutritional restriction conditions in BHI ‰ plates. FIG. 12 shows the results of the plate competition test on BHI of the studied species. It can thus be concluded that CECT 9174 secretes to the extracellular media one or more substances able to inhibit *S. mutans* growth.

Supernatant Inhibition Assay 2 to 3 colonies from a *S. mutans* CECT 479 and CECT 9174 pure culture in blood agar plate (Biomérieux) were taken and inoculated in 10 ml of THY broth (Todd-Hewit+ 5% yeast extract+5% foetal bovine serum) In 50 ml tubes (BD Falcon). The tubes were incubated under agitation at 35° C. and 100 rpm for 18 hours. After the incubation, both cultures were filtrated through a 0.22 μm to remove all cell rest. Afterwards, in both filtered broths, 2 to 3 *S. mutans* CECT 974 were inoculated, and incubated again under agitation at 35° C. and 100 rpm for 18 hours. To confirm the presence or absence of cell growth, 1 ml of each of broth were taken, and it was inoculated by flood in blood agar plate at 37° C. In CO$_2$ 5% atmosphere for 24 hours. FIG. 13 shows the design of the assay. *S. mutans* CECT 974 grows in the filtered broth of *S. mutans* CECT 974. However, CECT 9174 filtered broth is able to Inhibit the growth of *S. mutans* CECT 974 when this strain is inoculated therein. It can thus be concluded that CECT 9174 secretes to the medium one or more substances able to inhibit the growth of *S. mutans*.

Example 5. The Inhibitory Activity of S. CECT 9174 is not Affected by the Proteinase K Activity CECT 9174 produces a bacteriocin of the class IIb lactobin/cerein 7B family which is thermostable, is not affected by the effect of the proteinase k, and exert a clear activity against cariogenic and periodontal pathogens. In order to demonstrate that S. CECT 9174 is not affected by the proteinase K activity the following assay was carried out: After 24 hour of incubation in solid medium of the strains to be tested, 10-15 µl of proteinase K (70 µg/ml) and 10-15 µl of PBS were added to each side of the colonies. Subsequently, 5 µl of the right and left sensitive strains were inoculated, as described in Kreth J. et al. 2005 and Zhu L et al. 2012. After incubation at 37° C. for 24 hours the plates were visualized. The absence of haloes Indicates that the inhibition is caused by molecules of peptide nature. The FIG. 14 shows the results: (A) The inhibitory activity over *S. mutans* of CECT 9174 is not affected by the proteinase K since in both sides (right:PBS and the left:proteinase K) *S. mutans* Is inhibited by CECT 9174. In contrast, in the case of *S. dentisani*, the inhibitory effect over *S. mutans* is negatively affected by the proteinase k, as described in [López-López A, Camelo-Castillo A, Ferrer M D, Simon-Soro Á and Look at (2017) Health-Associated Niche Inhabitants as Oral Probiotics: The Case of *Streptococcus dentisani*. Front. Microbiol. 8: 379. doi: 10.3389/fmicb.2017.00379]. This result can be observed when (B) and (C) of the FIG. 14 are compared. In (B), PBS does not prevent the inhibitory activity of *S. dentisani* over *S. mutans*, whereas in (C), Proteinase K prevents the inhibitory activity of *S. dentisani* over *S. mutans*.

Example 6. Inhibition/Antagonism Study 5 ul of the strain CECT 9174 are inoculated at a concentration of 1 McFarland in 0.9% saline in BHI plates and incubated in a 5% CO2 atmosphere for 16 hours; after that time, the same amount of the microorganism under study was inoculated near the colony and incubated again at 37° C. in a 5% CO2 atmosphere for 32 h. As a growth control, 5 ul of each of the microorganisms tested are incubated in isolation. The result of the experiment can be seen in FIG. 15, wherein A) shows the inhibition assay and B) shows the growth control. As shown in FIG. 15, CECT 9174 inhibits: *S. pyogenes, S. pneumoniae, S. galactiae, S. aureus, S. warnerii, S. mutans*. This activity has not been described in *S. dentisani*.

Example 7. CECT 9174 Inhibition Over *Fusobacterium nucleatum*

To evaluate the inhibition of S. CECT 9174 in plaque against *Fusobacterium nucleatum* DMSZ 20482, a suspension of 0.3 McFarland of *F. nucleatum* was made in BHI plates (Conda) to obtain a "carpet like" growth. At the same time, 10 µL of S. CECT 9174 was deposited as a "button", and the inhibition zone was evaluated after incubation for 72 hours in an anaerobic atmosphere (10% H$_2$, 10% CO2, and balance N$_2$) at 37° C. S. As shown in FIG. 16, CECT 9174 was able to inhibit *F. nucleatum*.

The invention claimed is:

1. A method of providing an anti-microbial treatment to a subject in need thereof, the method comprising administering to the subject the bacterial strain deposited at the Colección Española de Cultivos Tipo (CECT) by Servicio Galego de Saúde (SERGAS), on Jul. 20, 2016, with accession number CECT 9174.

2. A method of treating an infectious disease of an oral cavity of a subject, the method comprising administering to the subject the bacterial strain deposited at the Colección Española de Cultivos Tipo (CECT) by Servicio Galego de Saúde (SERGAS), on Jul. 20, 2016, with accession number CECT 9174.

3. The method of claim 2, wherein the infectious disease of the oral cavity is caused by Gram positive and/or Gram negative bacteria.

4. The method of claim 2, wherein the infectious disease of the oral cavity is caries and/or periodontal disease.

5. A probiotic, medical food composition or functional food comprising the bacterial strain deposited at the Colecci6n Espanola de Cultivos Tipo (CECT) by Servicio Galego de Sande (SERGAS), on Jul. 20, 2016, with accession number CECT 9174; and processed food.

6. A method of improving oral health of a subject comprising administering to the subject the probiotic, medical food composition or functional food of claim 5.

7. An oral health composition that comprises the bacterial strain deposited at the Colección Española de Cultivos Tipo (CECT) by Servicio Galego de Saúde (SERGAS), on Jul. 20, 2016, with accession number CECT 9174, and at least one additional component having antibacterial activity against one or more bacterial species that cause oral infections selected from: an antimicrobial agent, an antibacterial strain, and an anti-cariogenic agent.

8. A method of treating an infectious disease of an oral cavity of a subject, the method comprising administering to the subject the probiotic, medical food composition or functional food of claim 5.

9. The method of claim 8, wherein the infectious disease of the oral cavity is caries and/or periodontal disease.

10. A method for preparing a supernatant comprising:
  a) culturing a deposited bacterial strain, which was deposited at the Colección Española de Cultivos Tipo (CECT) by Servicio Galego de Saúde (SERGAS), on Jul. 20, 2016, with accession number CECT 9174, thereby producing a culture,
  b) centrifuging the culture of step a), and
  c) recovering a supernatant obtained from the centrifuging of step b).

11. A method of treating an infectious disease of an oral cavity of a subject, the method comprising administering to the subject the supernatant prepared according to the method of claim 10.

12. The method of claim 11, wherein the infectious diseases of the oral cavity is caries and/or periodontal disease.

13. A method of treating an infectious disease of an oral cavity of a subject, the method comprising administering to the subject a pharmaceutical composition comprising the bacterial strain deposited at the Colección Española de Cultivos Tipo (CECT) by Servicio Galego de Saúde (SERGAS), on Jul. 20, 2016, with accession number CECT 9174; and a pharmaceutically acceptable carrier, diluent, and/or excipient.

14. The method of claim 13, wherein the infectious disease of the oral cavity is caries and/or periodontal disease.

15. A method of treating an infectious disease of an oral cavity of a subject, the method comprising administering to the subject the oral health composition of claim 7.

16. The method of claim 15, wherein the infectious disease of the oral cavity is caries and/or periodontal disease.

\* \* \* \* \*